(12) United States Patent
Teodor et al.

(10) Patent No.: US 12,045,227 B2
(45) Date of Patent: Jul. 23, 2024

(54) PROOF-OF-WORK FOR BLOCKCHAIN APPLICATIONS

(71) Applicant: University of York, York (GB)

(72) Inventors: Roxana Iuliana Teodor, York (GB); Peter Damian Ashton, York (GB); Siamak Fayyaz Shahandashti, York (GB); Ian Bancroft, York (GB)

(73) Assignee: University of York (GB)

( * ) Notice: Subject to any disclaimer, the term of this patent is extended or adjusted under 35 U.S.C. 154(b) by 379 days.

(21) Appl. No.: 17/413,301

(22) PCT Filed: Dec. 3, 2019

(86) PCT No.: PCT/GB2019/053418
§ 371 (c)(1),
(2) Date: Jun. 11, 2021

(87) PCT Pub. No.: WO2020/120933
PCT Pub. Date: Jun. 18, 2020

(65) Prior Publication Data
US 2022/0027352 A1    Jan. 27, 2022

(30) Foreign Application Priority Data

Dec. 12, 2018 (GB) .................................. 1820267
Mar. 15, 2019 (GB) .................................. 1903567

(51) Int. Cl.
*G16B 50/30* (2019.01)
*G06F 16/23* (2019.01)
(Continued)

(52) U.S. Cl.
CPC ......... *G06F 16/2379* (2019.01); *G16B 50/30* (2019.02); *H04L 9/0637* (2013.01);
(Continued)

(58) Field of Classification Search
CPC ..... G06F 16/2379; G06F 21/64; G16B 50/30; H04L 9/0637; H04L 9/3236; H04L 9/3239; H04L 9/3247; H04L 9/3297; H04L 9/50
See application file for complete search history.

(56) References Cited

U.S. PATENT DOCUMENTS 9,521,126 B2 * 12/2016 Yarvis ................. H04L 63/0442
11,652,650 B1 * 5/2023 Teodor ................. H04L 9/3297
713/193
(Continued)

FOREIGN PATENT DOCUMENTS

CA          3040147 A1 *   4/2018  ......... G06F 16/2282

OTHER PUBLICATIONS

Ball, Marshall, et al. "Proofs of useful work." Cryptology ePrint Archive (2017). (Year: 2017).*
(Continued)

*Primary Examiner* — Michael Simitoski
(74) *Attorney, Agent, or Firm* — Baker Botts L.L.P.

(57) ABSTRACT

Methods, computing apparatuses, computer readable media and systems are described that are for use with blockchain applications. An authority server may communicate a data package to a mining node. The mining node may receive the data package from the authority server, the data package comprising a plurality of datasets, each dataset comprising signal information. The mining node may analyse the data package to convert the signal information of each dataset to a corresponding data output. The mining node may communicate the plurality of data outputs to an authority server and, upon verification of the plurality of data outputs, the plurality of data outputs may be used in establishing a proof-of-work for appending a block record to a blockchain. Encryption and decryption methods may be used to secure data according to methods described herein. In some (Continued)

examples, the signal information of each dataset relates to a polynucleotide sequence and the corresponding data output relates to a read.

19 Claims, 12 Drawing Sheets

(51) Int. Cl.
  *H04L 9/00* (2022.01)
  *H04L 9/06* (2006.01)
  *H04L 9/32* (2006.01)
(52) U.S. Cl.
  CPC .......... *H04L 9/3236* (2013.01); *H04L 9/3247* (2013.01); *H04L 9/3297* (2013.01); *H04L 9/50* (2022.05)

(56) References Cited

U.S. PATENT DOCUMENTS

| | | | | |
|---|---|---|---|---|
| 2016/0085916 | A1* | 3/2016 | Smith | G16H 50/70 705/3 |
| 2017/0243212 | A1* | 8/2017 | Castinado | G06Q 20/389 |
| 2017/0359170 | A1* | 12/2017 | Bower, III | H04L 9/0894 |
| 2017/0359374 | A1* | 12/2017 | Smith | H04L 9/3236 |
| 2018/0068060 | A1 | 3/2018 | Ceze et al. | |
| 2019/0214111 | A1* | 7/2019 | Alberti | G16B 50/40 |
| 2019/0352709 | A1* | 11/2019 | Clarke | G01N 33/48721 |
| 2021/0271982 | A1* | 9/2021 | Lee | G06N 3/123 |

OTHER PUBLICATIONS

Oliver, Carlos G., Alessandro Ricottone, and Pericles Philippopoulos. "Proposal for a fully decentralized blockchain and proof-of-work algorithm for solving NP-complete problems." arXiv preprint arXiv:1708.09419 (2017). (Year: 2017).*

A. Shoker, "Sustainable blockchain through proof of exercise," 2017 IEEE 16th International Symposium on Network Computing and Applications (NCA), Cambridge, MA, USA, 2017, pp. 1-9, doi: 10.1109/NCA.2017.8171383. (Year: 2017).*

Zhang, Fan, et al. "{REM}:{Resource-Efficient} Mining for Blockchains." 26th USENIX Security Symposium (USENIX Security 17). 2017. (Year: 2017).*

Ozercan, Halil Ibrahim, et al. "Realizing the potential of blockchain technologies in genomics." Genome research 28.9 (2018): 1255-1263.

Ileri, Atalay M., et al. "Coinami: a cryptocurrency with DNA sequence alignment as proof-of-work." arXiv preprint arXiv:1602.03031 (2016).

Russian application No. 2021120064, Search Report completed Jun. 23, 2023, 4 pages.

* cited by examiner

PROOF-OF-WORK FOR BLOCKCHAIN APPLICATIONS

CROSS-REFERENCE TO RELATED APPLICATION

The present application is a U.S. National Stage Application of International Application No. PCT/GB2019/053418 filed Dec. 3, 2019 which claims priority to United Kingdom Patent Application No. 1903567.4 filed Mar. 15, 2019 and United Kingdom Patent Application No. 1820267.1 filed Dec. 12 2018, all of which are incorporated herein by reference in their entirety for all purposes.

TECHNICAL FIELD

The present disclosure relates to data processing and in particular to blockchain implementations. More particularly, the present disclosure relates to methods and apparatuses which can be used in appending a block record to a blockchain.

BACKGROUND

A blockchain, sometimes known as a distributed ledger or a distributed consensus ledger, is a type of distributed database. A blockchain enables tamper-resistant and decentralised storage of data. A copy of the ledger/blockchain can be stored on each of multiple nodes of a blockchain network.

A blockchain comprises a plurality of block records, also known as blocks or data structure blocks. A block record of a blockchain typically comprises payload data (i.e. the data recorded in that block record for storage in the blockchain), a unique identifier of a preceding block record of the blockchain, and a proof-of-work (POW). When a block record is added to the blockchain, copies of the new block/blockchain are distributed to other nodes of the blockchain network, which can verify the work done to append the new block and accept the update to the blockchain or can disregard the new block if the associated work cannot be verified.

A block record typically comprises payload data in the form of data and/or computer-executable instructions. In this way, if the blockchain is used, for example, to record instructions such as transactions, then a complete history of transactions can be established on the ledger. Each transaction is a data structure that encodes the transfer of control of a digital asset from one party of a blockchain system to another. If the blockchain is used, for example, to record computer-executable instructions (often referred to as a "smart contract"—a computerized protocol that executes the terms of a machine-readable contract or agreement) then function calls to the computer-executable instructions can be used to initiate a computer-executable process. A smart contract can process inputs in order to produce results, which can then cause actions to be performed based on those results.

Each block record typically contains a link to a preceding block record, for example, a hash value of the information in the preceding block record or a hash value of a header of the previous block record. The hash value is typically determined by using the information of the preceding block as part of the input to a hash function which outputs the hash value. Each block record links back to the preceding block record. In this way, once validated, a block record will be linked to a preceding block record and, through that preceding block record, to each earlier block record in turn back to a genesis block record—the only block record which does not contain a link to a preceding block record. Although the hash value is typically simple to compute, there may be one or more validity requirements imposed on the hash value. In addition, the hash value is normally based on a special type of mathematical function that is not reversible and so one cannot readily know which input will give a desired output without trialling numerous inputs.

Each block record typically also comprises a proof-of-work (POW). A POW is a piece of data which is difficult to produce but easy for others (that is, other users or other computing devices) to verify and which satisfies certain validity requirements. Each block record thereby provides trustable, reliable evidence that work has been done generating it. That work may be, for example an expenditure of a significant amount of processing resources such as the time taken to compute some output.

The integrity of payload data stored in the blockchain is ensured because each block record links to a preceding block record and because in order to tamper with payload data in a block record of the blockchain, a tampering party would have to do further work to store the tampered block and each subsequent block on the blockchain, which is infeasible while the majority of nodes of the blockchain network are each checking the validity of the blockchain and adding their own block records.

Within some blockchain implementations, such as the popular "Bitcoin", each block includes a header having a hash value for the previous block. To create a new block, a miner must find a nonce value which, when included as part of the input to the hash function, results in a hash value which meets a certain validity requirement, in particular a hash value that is below a predetermined threshold value. A miner typically guesses a nonce value and then checks that, when the guessed nonce value is combined with other fixed data including the hash of the preceding block and input into the hash function, the hash function outputs a hash value that is below the predetermined threshold value. In this way, the miner does work in expending computational resources to find a suitable nonce value satisfying a validity requirement. Once found, a second miner can check that a particular block is valid by inputting the same information including the declared nonce value into the hash function and checking that the output is valid. In such blockchain implementations, the declared nonce thus serves as a proof-of-work for the relevant block.

The present disclosure relates to systems, methods and apparatuses that use alternative proofs-of-work to append a block to a blockchain.

SUMMARY

The inventors have recognised that the nonce-guessing used to establish a proof-of-work (POW) of many blockchain implementations is wasteful and requires expenditure of enormous computational resources to solve mathematical puzzles with no practical use to mankind beyond their role as POW. The inventors have devised a blockchain implementation in which nonce-guessing is replaced with "useful" work.

Proof-of-work schemes may serve two general purposes, namely to maintain the difficulty of appending a block record to a blockchain (and thereby contributing to the security of the blockchain) and for allowing one to check the validity of a given block record. In most blockchain implementations, for which the proof-of-work is based on e.g. nonce guessing, the entire blockchain network is completely decentralised in that each mining node of the network is able to perform the required work (e.g. guessing a nonce), and demonstrate the proof-of-work (e.g. announcing the declared nonce with the completed block when the hash function and threshold hash value is known to the rest of the blockchain network) without involving a second server/computing device. In contrast, in the implementations disclosed herein, one or more parties, referred to herein as authority servers, are used to feed in work assignments in the form of data packages to be processed by mining nodes of a blockchain network.

As used in the present specification and in the appended claims, the terms "node" or "computing device" or "computing apparatus" are meant to be understood broadly as any hardware device, virtual device, group of hardware devices, group of virtual devices, or combination thereof within a network. Nodes may include, for example, servers, switches, data processing devices, data storage devices, load balancers, routers, and virtual embodiments thereof, among many other types of hardware and virtual devices.

A "mining node" as used herein is a node of the blockchain network that is involved in mining, the process of doing work in order to append a block to the blockchain. A collection of mining nodes working on the same blockchain implementation may be referred to as a "mining network".

The term "blockchain network" as used herein is understood to mean the nodes which take part in the sharing, storing and/or establishment of the blockchain. Accordingly, while each mining node is part of a blockchain network, an authority server may or may not be part of the blockchain network. A mining network may be a subnetwork of a blockchain network. For example, a blockchain network may contain a mining network and one or more further peer-to-peer connected elements not involved in the mining process itself (for example, storage devices containing copies of the blockchain, gatekeeping servers that only validate blocks of the blockchain and forward on any validated blocks and so on).

A method is disclosed herein for appending a block record to a blockchain stored on mining nodes of a network. A block record comprises payload data, a proof-of-work, and a unique identifier of a preceding block record of the blockchain. The method comprises receiving a data package from an authority server. The data package comprises a plurality of datasets. Each of the plurality of datasets comprises signal information. The method further comprises analysing the data package to convert the signal information of each dataset to a corresponding data output. The method further comprises communicating the plurality of data outputs to an authority server, the plurality of data outputs for use in establishing a proof-of-work for appending a block record to the blockchain.

Advantageously, such a method enables a blockchain to be implemented using a proof-of-work scheme in which a mining node performs useful work coordinated by one or more authority servers or a central authority server. In particular, the work comprises the conversion of the signal information of each dataset of a received data package to a corresponding data output. The data outputs are communicated to an authority server (which may be the same authority server or a different authority server to that from which the data package was initially received) and used in establishing a proof-of-work for appending a block record to the blockchain.

The method may further comprise receiving a signed token from an authority server. The method may further comprise creating a block record for the blockchain using the signed token as the proof-of-work. The method may further comprise communicating the created block record to at least a mining node of the network. In this way, a mining node may receive a POW in the form of a signed token from an authority server, create the block, and communicate the block record to at least a mining node of the network which may then accept or reject the block record based on a check of the POW.

The signed token may comprise a signed hash of the analysed data package. In this way, the signed token may be intrinsically linked to the specific work performed by the mining node. The signed hash may be signed, for example, using the authority server's private key of a public-private key pair. The signed token may comprise further information such as, for example, the identity of the mining node which analysed the data package. The signed token may comprise, for example, the identity of the work package(s) from which the data outputs were derived. The signed token may comprise, for example, the version of the data transformation software used to generate the results. The signed token may comprise, for example, the date and time that the mining node submitted the results.

Analysing a data package to convert signal information to a corresponding data output may comprise any suitable processing, for example, the performance of a "base calling" algorithm. Analysing may comprise the use of a variational autoencoder or trained neural network. For example, a mining node may compress the received signal information into a latent space representation.

Creating a block record for the blockchain may include consulting a version of the blockchain stored in one or more machine readable storage media to read, extract or otherwise determine the unique identifier of the preceding block of the blockchain. Creating a block record for the blockchain may further comprise retrieving payload data from a data pool of unprocessed payload data.

In one or more other embodiments, a mining node may communicate the plurality of data outputs and also the payload data and other contents of the block record, to an authority server. In such embodiments, the authority server may be the entity that creates the block record having verified the data outputs. That is, the authority server may or may not communicate the signed token to the mining node, and may create the block record itself. The authority server may be the entity that communicates the block record. The authority server may therefore be part of the blockchain network itself.

The term "data broker" is another name for an authority server.

The data package comprises a plurality of datasets, each of the plurality of datasets comprising signal information. The work performed comprises analysing the data package to convert the signal information of each dataset to a corresponding data output. Such conversion of signal information to data outputs can be useful in many applications such as biological analysis. As an example, the work performed may comprise analysing signal information in the form of CT-scan or MRI data to convert that signal information to a corresponding data output such as 3D printing data. As another example, the work performed may comprise analysing images, for example microscopy images, to determine a data output.

The signal information of each dataset may be representative of a polynucleotide sequence. Converting the signal information of each dataset to a corresponding data output may comprise converting the signal information of each dataset to a corresponding read, each read of the plurality of reads describing the respective polynucleotide sequence. Such a process is often referred to as "base calling". Communicating the plurality of data outputs to an authority server may comprise communicating the plurality of reads to an authority server.

The polynucleotide sequence may comprise a deoxyribonucleic acid, DNA, sequence or a ribonucleic acid, RNA, sequence.

Advantageously, by providing a method in which the signal information of each dataset is representative of a polynucleotide sequence, and in which converting the signal information to a corresponding data output comprises converting the signal information to a corresponding read describing the respective polynucleotide sequence, a very time and resource-intensive calculation for polynucleotide sequencing is performed in order to append a block record to a blockchain.

The skilled person would appreciate that converting signal information to a data output such as a read is very different to, for example, "read mapping", in which a read is compared to a reference read. In read mapping, individual reads are aligned to a reference sequence, whether the reference is a complete genome, transcriptome, or de novo assembly.

"Base calling" is a term used to describe a process of determining a nucleobase sequence from signal information, such as a characteristic current signal. There are many types of possible signals depending on which sequencer is used to attempt to read the nucleobases. One useful sequencer is a nanopore sequencer.

Transmembrane pores (e.g. nanopores) have been used to identify small molecules or folded proteins and to monitor chemical or enzymatic reactions at approximately the single molecule level. Such transmembrane pores have great potential as electrical biosensors for polymers and a variety of small molecules. Nanopore sequencers are useful for polynucleotide sequencing and biomarker recognition.

Ion flow (for example, electron flow/current) through a nanopore may be measured under a potential difference applied across the nanopore. Interaction of an analyte with the nanopore can give rise to a characteristic change in ion flow (for example, a characteristic current profile) as the analyte translocates through the nanopore. This raw data in the form of ion flow/current signal information can be used to characterise the analyte. For example, a polynucleotide strand such as DNA may pass through the nanopore sequencer. DNA comprises nucleobases (cytosine, guanine, adenine and thymine) and, as a DNA segment passes through the nanopore sequencer, a resultant characteristic current profile will be produced depending on which of the nucleobases is passing through the sequencer at any given moment.

Signal information produced by a sequencer (a nanopore sequencer or otherwise) is typically very noisy due to, for example, multiple nucleotides passing through the sequencer at the same time, the analyte passing through the sequencer at an inconsistent rate and so on. Accordingly, the task of determining a polynucleotide sequence (i.e. determining a "read") from the signal information is a computationally intensive task to complete.

Signal information representative of a polynucleotide sequence may comprise raw data produced by a nanopore sequencer.

Signal information representative of a polynucleotide sequence may comprise current information corresponding to current flow through a nanopore and a polynucleotide translocating through the nanopore.

A unique identifier of a preceding block record of the blockchain may comprise a hash of the preceding block record of the blockchain or a hash of a header of the preceding block of the blockchain.

The payload data may comprise at least one of transaction data or a smart contract.

The receiving a data package from an authority server may be in response to requesting a data package from an authority server. For example, a mining node may begin a process of appending a block record to a blockchain by requesting the data package from the authority server. Advantageously, this may enable a mining node to connect to or drop out of the blockchain network, doing work only when connected to the wider blockchain network and when such work is intended to be completed.

The authority server may or may not be a mining node of the network.

Computing apparatus is disclosed herein for appending a block record to a blockchain stored on mining nodes of a network, the block record containing payload data, a proof-of-work, and a unique identifier of a preceding block of the blockchain. The computing apparatus comprises one or more processors. The computing apparatus further comprises one or more machine readable storage media having instructions stored thereon which, when processed by the one or more processors, cause the one or more processors to receive a data package from an authority server, the data package comprising a plurality of datasets, wherein each of the plurality of datasets comprises signal information. The instructions, when processed by the one or more processors, further cause the one or more processors to analyse the data package to convert the signal information of each dataset to a corresponding data output. The instructions, when processed by the one or more processors, further communicate the plurality of data outputs to an authority server, the plurality of data outputs for use in establishing a proof-of-work for appending a block record to the blockchain.

A method is provided herein for performance by an authority server, the authority server trusted by mining nodes of a network to authenticate a block record of a blockchain. The method comprises receiving information containing a first plurality of data outputs from a first mining node of the network, each data output of the first plurality of data outputs determined from a first data package analysed by the first mining node, the first data package comprising a plurality of data sets. The method further comprises verifying the first plurality of data outputs. The method further comprises, in response to verifying the first plurality of data outputs, digitally signing a unique token to be used as proof-of-work in a block record of the blockchain.

Advantageously, an authority server performing such a method outsources the computational task of converting datasets of a data package into data outputs to a mining node. As the authority server is trustable by several mining nodes of a blockchain network, a signed token from the authority server that validates the work done by a first mining node can be used as proof-of-work in a block record of a blockchain. The signed token may be used by other nodes of the blockchain network to verify that a block record added by the first mining node is valid.

The method may further comprise sending the signed token to the first mining node to be used as proof-of-work in the block record of the blockchain. In this way, the first mining node is enabled to create the block record. In one or more alternative embodiments, the authority server itself may sign the token, create the block record from data received from the mining node, and communicate the created block to the blockchain network.

Verifying the first plurality of data outputs may comprise determining that a corroboration condition has been met. For example, the first plurality of data outputs may be compared with previously computed data outputs received from at least another mining node and stored in memory accessible by the authority server. Alternatively, the first plurality of data outputs may be compared with further data outputs previously and/or subsequently received from further mining nodes. In some embodiments, the authority server may communicate with other authority servers to check whether corroborating data outputs have been sent to those other authority servers.

Determining that the corroboration condition has been met may comprise determining that each data output of the first plurality of data outputs has been corroborated by a threshold number of further mining nodes of the network. Determining that each data output of the first plurality of data outputs has been corroborated by a threshold number of further mining nodes of the network may comprise comparing the first plurality of data outputs with one or more further pluralities of data outputs, each of the one or more further pluralities of data outputs received from a corresponding further mining node of the network. The further pluralities of data outputs may have been determined from further data packages analysed by the corresponding further mining nodes, the further data packages each containing a plurality of datasets each comprising signal information, one or more datasets overlapping with those comprised within the first data package.

The authority server may therefore produce data packages comprising a plurality of datasets, the plurality of datasets related to several subjects. For example, a data package may comprise a first dataset comprising signal information representative of a part of a polynucleotide sequence of a first subject such as a plant specimen, a second dataset comprising signal information representative of a part of a polynucleotide sequence of a second subject such as a cat specimen, and further datasets comprising signal information representative of parts of further polynucleotide sequences of further people, creatures, plants and so on. That is, the datasets within each data package may comprise signal information generated from multiple sources. The authority server may send a first data package to the first mining node, a second data package to a second mining node and so on. If one or more datasets within the first and second data packages overlap then the data outputs from the second mining node can be used to verify the data outputs from the first mining node and vice versa. However, if no data packages are identical or overlap then it is infeasible for any minority number of mining nodes to accumulate enough information to reproduce a complete set of data outputs for any particular user. For example, if a characteristic profile current of a DNA sequence is produced using a nanopore sequencer for a human subject, that characteristic current profile may be divided up into multiple datasets, each dataset comprising a part of the current signature. A mining node may receive a data package comprising one dataset relevant to that human subject out of all of the relevant data packages, and that one dataset may be one of many datasets (relating to different subjects) comprised in the data package. Furthermore, the data package may contain no further identifying information as to the subject to which each dataset relates. Accordingly, if the number of datasets relating to each subject is large, and the number of mining nodes in a blockchain network is large, then it is highly infeasible for a mining node or a minority number of mining nodes to determine, for example, the entire DNA sequence for that human subject. Advantageously, this greatly increases data privacy and security for subjects of any information included in data packages. An identifier of a nanopore sequencer that generated the signal information of a particular data item can be included in a signed token or elsewhere in a block of the blockchain.

Determining that each data output of the first plurality of data outputs has been corroborated by a threshold number of further mining nodes of the network may comprise determining that each data output of the first plurality of data outputs has been corroborated within a predefined error threshold by a threshold number of further mining nodes of the network. Advantageously, allowing minor discrepancies between data outputs helps to account for errors produced in converting signal information into data outputs. Such discrepancies may occur due to, for example, the noisiness of the signal information. For example, when the signal information is representative of a polynucleotide sequence, depending on the method by which such signal information was generated, identical datasets may be converted to largely similar data outputs by different mining nodes.

Receiving the information containing the first plurality of data outputs may be in response to communicating a data package to the first mining node, the data package comprising a plurality of datasets, wherein each of the plurality of datasets comprises signal information for conversion to a data output. Communicating the data package to the first mining node may be in response to receiving a request for a data package from the first mining node.

The method may further comprise, prior to communicating the first data package to the first mining mode, receiving multiple pre-processed data items from multiple data sources. The method may further comprise, prior to communicating the first data package to the first mining node, dividing the multiple pre-processed data items into independently processable datasets. The method may further comprise, prior to communicating the first data package to the first mining node, packaging a selection of the independently processable datasets into a data package. The method may further comprise, prior to communicating the first data package to the first mining node, storing metadata concerning which independently processable datasets are included in the data package, optionally including the source of the data package, the date and time of submission and any other data stored in the data package which is not required for transformation of the data (e.g., identity of the sequencing equipment, date and time the sequencer was run, names of the biological samples as provided by the submitting user).

As explained previously, such method features help to ensure data privacy and data security for the data provided by the multiple data sources. The skilled person would appreciate that the term "data source" should be interpreted broadly. A "data source" may comprise, for example, a computing device comprising a database of signal information. The data source may store information relating to several problems, subjects (for example several patients) or issues. A data source may comprise a user's computer device and the user may provide a data item to the authority server, for example. A user may be, for example, a research institute, hospital, government organisation or individual person.

The first data package analysed by the first mining node may also comprise decoy datasets. Verifying the first plurality of data outputs may include checking decoy data outputs of the first plurality of data outputs against a local register of data outputs. Such decoy datasets may further enable an authority server to check that a mining node is not attempting to cheat when undertaking work to append a block to a blockchain.

A server, or authority server, is disclosed herein. The authority server is trusted by mining nodes of a network to authenticate a block record of a blockchain. Each mining node comprises computing apparatus for appending a block record to the blockchain. The authority server comprises one or more processors. The authority server further comprises one or more memory units, the memory units having instructions stored therein which, when processed by the one or more processors, cause the one or more processors to receive information containing a first plurality of data outputs from a first mining node of the network, each data output of the first plurality of data outputs determined from a first data package analysed by the first mining node, the data package comprising a plurality of data sets. The instructions, when processed by the one or more processors, further cause the one or more processors to verify the first plurality of data outputs. The instructions, when processed by the one or more processors, further cause the one or more processors to, in response to verifying the first plurality of reads, digitally sign a unique token to be used as proof-of-work in a block record of the blockchain.

A system is disclosed herein for processing signal information as proof-of-work for appending a block record to a blockchain. The system comprises one or more authority servers, each comprising one or more processors. The system further comprises a network of mining nodes, wherein each mining node comprises one or more processors. A mining node is configured to receive a data package from an authority server, the data package comprising a plurality of datasets, wherein each of the plurality of datasets comprises signal information. The mining node is further configured to analyse the data package to convert the signal information of each dataset to a corresponding data output. The mining node is further configured to communicate the plurality of data outputs to an authority server. The mining node is further configured to receive a signed token from an authority server. The mining node is further configured to create a block record for the blockchain using the signed token as the proof-of-work. The mining node is further configured to communicate the created block record to at least a second mining node of the network. An authority server is configured to receive information containing the plurality of data outputs from the mining node. The authority server is further configured to verify the plurality of data outputs. The authority server is further configured to, in response to verifying the plurality of data outputs, digitally sign a unique token. The authority server is further configured to send the signed token to the mining node to be used as proof-of-work in a block record of the blockchain.

A system is disclosed for processing polynucleotide sequence data as proof-of-work for appending a block record to a blockchain. The system comprises one or more authority servers, each comprising one or more processors. The system further comprises a network of mining nodes, wherein each mining node comprises one or more processors. A mining node is configured to receive a data package from an authority server, the data package comprising a plurality of datasets, wherein each of the plurality of datasets comprises signal information representative of a polynucleotide sequence. The mining node is further configured to analyse the data package to convert the signal information of each dataset to a corresponding read, each read of the plurality of reads describing the respective polynucleotide sequence. The mining node is further configured to communicate the plurality of reads to an authority server. The mining node is further configured to receive a signed token from an authority server. The mining node is further configured to create a block record for the blockchain using the signed token as the proof-of-work. The mining node is further configured to communicate the created block record to at least a second mining node of the network. The authority server is configured to receive information containing the plurality of reads from the mining node. The authority server is further configured to verify the plurality of reads. The authority server is further configured to, in response to verifying the first plurality of reads, digitally sign a unique token. The authority server is further configured to send the signed token to the mining node to be used as proof-of-work in a block record of the blockchain.

Computing apparatus is disclosed herein for appending a block record to a blockchain stored on mining nodes of a network, the block record comprising payload data, a proof-of-work, and a unique identifier of a preceding block of the blockchain. The computing apparatus comprises one or more processors. The computing apparatus further comprises one or more machine readable storage media having stored thereon a first set of instructions for processing a data package received from an authority server, the first set of instructions requiring an encryption key. The computing apparatus further comprises one or more machine readable storage media having stored thereon a second set of instructions which, when processed by the one or more processors, implement the step of receiving a data package from an authority server, the data package comprising an encryption key and a plurality of datasets, each of the plurality of datasets comprises signal information. The second set of instructions, when processed by the one or more processors, further implement the step of processing the first set of instructions using the received encryption key, to convert the signal information of each dataset to a corresponding encrypted data output. The second set of instructions, when processed by the one or more processors, further implement the step of communicating the plurality of encrypted data outputs to an authority server, where the plurality of encrypted data outputs for use in establishing a proof-of-work for appending a block record to the blockchain.

A method is provided herein. The method is for performance by a mining node having computer-readable instructions to process a data package received from an authority server, the instructions requiring an encryption key. The method comprises receiving a data package from an authority server, the data package comprising an encryption key and a plurality of datasets, wherein each of the plurality of datasets comprises signal information. The method further comprises using the received encryption key, performing the computer-readable instructions to convert the signal information of each dataset to a corresponding encrypted data output. The method further comprises communicating the plurality of data outputs to an authority server, the plurality of data outputs for use in establishing a proof-of-work for appending a block record to the blockchain.

Advantageously, a mining node performing such a method may not ever have access to decrypted data outputs and so may never be able to determine a subject matter to which the datasets relate. Accordingly, the method leads to increased data privacy for users submitting the original data items, as the mining node is less able to determine information about the original data items.

A method is provided herein. The method is for performance by one or more authority servers. The method comprises receiving data items from multiple data sources, the data items comprising signal information. The method further comprises dividing the data items into independently processable datasets. The method further comprises generating an encryption key and corresponding decryption key. The method further comprises collecting a selection of the independently processable datasets and the encryption key into a data package, the independently processable datasets of the data package being from multiple data sources. The method further comprises communicating the data package to a mining node of a blockchain mining network to convert the signal information of each dataset to a corresponding encrypted data output. The method further comprises receiving information containing a plurality of encrypted data outputs and decrypting the encrypted data outputs using the generated decryption key.

Advantageously, an authority server performing such a method can outsource the computational task of converting datasets of a data package into data outputs to a mining node. The encryption key generated by the authority server also ensures that the mining node is less able to determine information about the nature of the original data item. Furthermore, intercepting third parties are also less able to determine information about the original data items. This leads to increased data privacy.

The encryption key may comprise a distinct encryption key for each dataset of the data package. The encrypted data outputs may comprise sequence of letters and decrypting the encrypted data outputs may comprise substituting the letters for IUPAC nucleotide codes. An IUPAC nucleic acid code is to be understood as a nucleic acid notation as formalized by the International Union of Pure and Applied Chemistry (IUPAC). Other notations may also be used. The encrypted data output may include decoy features and decrypting the encrypted data outputs may comprise removing the decoy features.

The method may further comprise verifying the decrypted data outputs, and in response to verifying the decrypted data outputs, digitally signing a unique token to be used as proof-of-work in a block record of the blockchain. The method may further comprise communicating the verified decrypted outputs to authorised users.

The signal information of at least one of the data items may comprise raw data produced by a nanopore sequencer, and the signed token may include an identifier of the nanopore sequencer. The signal information of at least some of the data items may be representative of a polynucleotide sequence, and the decrypted data outputs may comprise corresponding sections of polynucleotide sequences. The polynucleotide sequences may comprise a deoxyribonucleic acid, DNA, sequence or a ribonucleic acid, RNA, sequence.

An authority server is disclosed herein. The authority server comprises one or more processors. The authority server further comprises one or more memory units, the memory units having instructions stored therein which, when processed by the one or more processors, cause the one or more processors to divide received data items into independently processable datasets, the data items received from multiple data sources, the data items comprising signal information. The instructions, when processed by the one or more processors, further cause the one or more processors to generate an encryption key and corresponding decryption key. The instructions, when processed by the one or more processors, further cause the one or more processors to collect a selection of the independently processable datasets and the encryption key into a data package, the independently processable datasets of the data package being from multiple data sources. The instructions, when processed by the one or more processors, further cause the one or more processors to communicate the data package to a mining node of a blockchain mining network to convert the signal information of each dataset to a corresponding encrypted data output. The instructions, when processed by the one or more processors, further cause the one or more processors to process received information, the received information containing a plurality of encrypted data outputs, wherein processing the received information comprises decrypting the encrypted data outputs using the generated decryption key.

A computer readable medium is described herein. The computer readable medium has instructions stored thereon, which when executed by a processor, causes the processor to perform a method as described herein. The computer-readable medium may be a non-transitory computer-readable medium.

A computer program and/or the code/instructions for performing such methods as described herein may be provided to an apparatus, such as a computer, on a computer readable medium or computer program product. The computer readable medium could be, for example, an electronic, magnetic, optical, electromagnetic, infrared, or semiconductor system, or a propagation medium for data transmission, for example for downloading the code over the Internet. Alternatively, the computer readable medium could take the form of a physical computer readable medium such as semiconductor or solid-state memory, magnetic tape, a removable computer diskette, a random access memory (RAM), a read-only memory (ROM), a rigid magnetic disc, and an optical disk, such as a CD-ROM, CD-R/W or DVD.

Many modifications and other embodiments of the inventions set out herein will come to mind to a person skilled in the art to which these inventions pertain in light of the teachings presented herein. Therefore, it will be understood that the disclosure herein is not to be limited to the specific embodiments disclosed herein. Moreover, although the description provided herein provides example embodiments in the context of certain combinations of elements, steps and/or functions may be provided by alternative embodiments without departing from the scope of the invention.

BRIEF DESCRIPTION OF THE FIGURES

Embodiments of the invention will now be described by way of example only, with reference to the accompanying figures, in which.

Throughout the description and the drawings, like reference numerals refer to like parts.

DETAILED DESCRIPTION

Figure 1A:
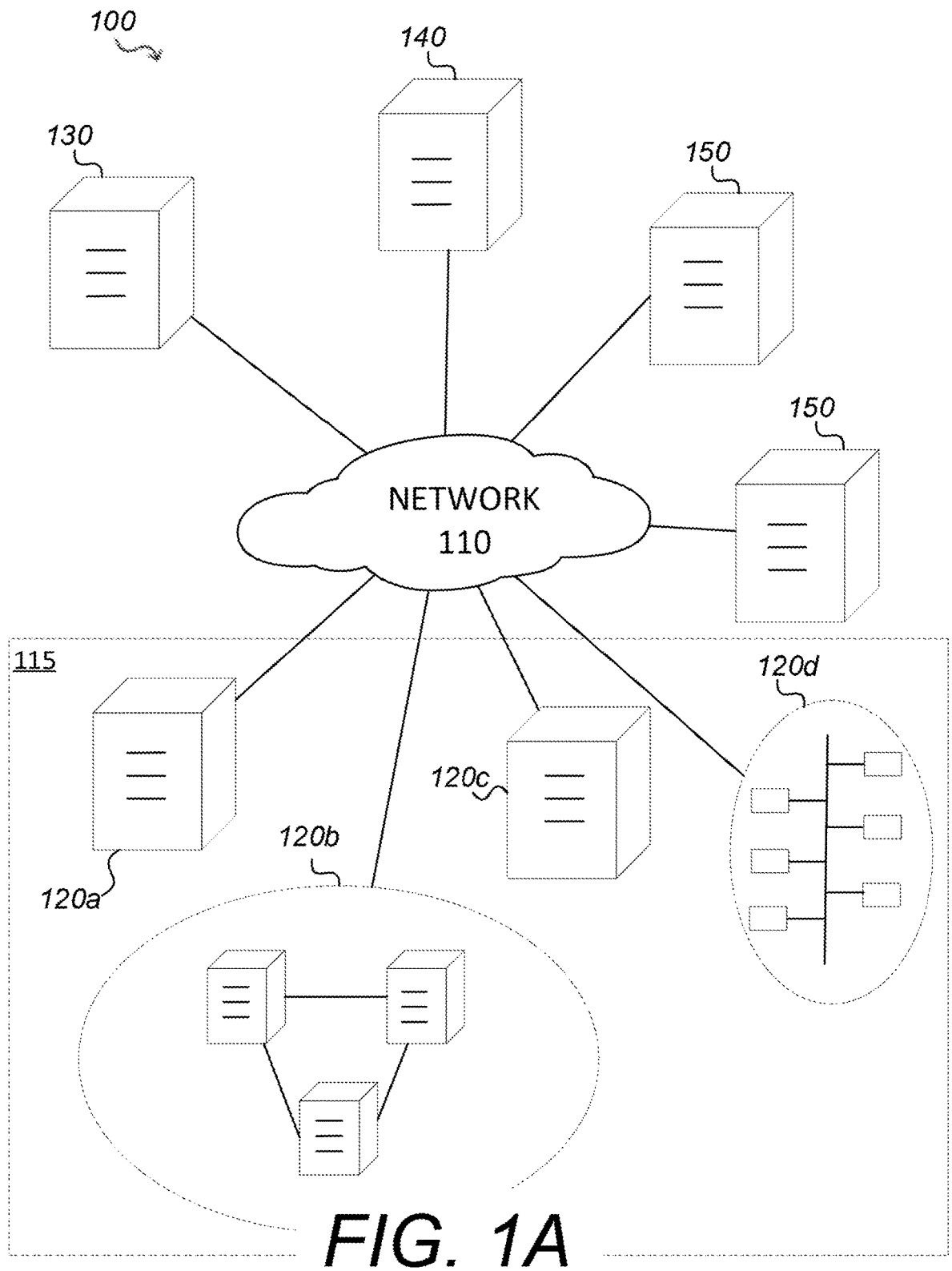
FIG. 1A shows a communications system for supporting a blockchain implementation.

Whilst various embodiments are described below, the invention is not limited to these embodiments, and variations of these embodiments may well fall within the scope of the invention which is to be limited only by the appended claims.

As described above, a blockchain is a type of database comprising linked block records/blocks of data validated and stored on multiple nodes of a blockchain network. A block record of a blockchain typically comprises payload data (i.e. the data recorded in that block record for storage in the blockchain), a unique identifier of a preceding block record of the blockchain (for example a hash value representative of information contained in that preceding block), and a proof-of-work (POW).

The term "payload data" as used herein is understood broadly to include the data and/or computer-executable instructions (e.g. smart contracts) recorded or to be recorded on a blockchain. For example, payload data may relate to transfers of a cryptocurrency from one party to another.

Each block record typically contains a link to a preceding block record, for example, a hash value of the information in the preceding block record or a hash value of a header of the previous block record. Each block record typically also comprises a proof-of-work (POW). A POW is a piece of data which is difficult to produce but easy for others (that is, other users or other computing devices) to verify and which satisfies certain validity requirements. Each block record thereby provides trustable, reliable evidence that work has been done generating it. That work may be, for example an expenditure of a significant amount of processing resources such as the time taken to compute some output.

A PoW system (or protocol or function) is useful for a consensus based blockchain implementation. A mining node is required to undertake some work, converting a plurality of datasets each comprising signal information into a plurality of data outputs. Other parties including mining nodes can independently check for some verification, such as a signed token from a trusted authority server, that work was genuinely performed before determining whether to accept or disregard a block from that mining node. Furthermore, each mining node may accept the longest valid blockchain as the most up-to-date (and attempt to append subsequent block records to that longest valid blockchain) and disregard shorter chains. In this way, requiring a mining node to do significant work to append a block record to a blockchain ensures that, if any node attempts to tamper with an earlier block record, they would need to perform significant work to affix the tampered block record validly onto the chain and enough subsequent block record to overtake the current longest chain in order for the majority of nodes to accept the tampered blockchain.

A block record may further comprise one or more of a timestamp indicating when a first mining node submitted a processed data package (i.e. a plurality of data outputs) to an authority server for verification, an identifier of the first mining node that submitted the processed data package to the authority server, a timestamp indicating when an authority server received the data outputs, an indicator as to which authority server verified the data outputs, a timestamp indicating when the processed data package was verified by an authority server, a reference number of the data package processed by the mining node, or any other relevant information.

FIG. 1A depicts a communication system 100 that may include a communication network 110, several mining nodes 120 (shown in FIG. 1A as mining nodes 120a-120d), an authority server 130, a central authority server 140 and multiple data sources 150. Communication network 110 may be any suitable communication network, such as the Internet.

The mining nodes 120 may take any suitable form and may comprise any suitable computing apparatus for performing a method as described herein. For example, mining nodes 120a and 120c are shown as computers or servers and may be any suitable computing devices capable of processing and storage, such as a personal computer, a server, a laptop computer, or other such machine. Mining node 120b is shown as a mining pool or collection or cluster of interconnected computing devices, such as a collection of servers or personal computers, which are configured to collectively perform methods as described herein by, for example, parallel processing of data or by dividing up the tasks of the methods described herein amongst themselves. The collection of computing devices may communicate with one another via a direct, peer-to-peer connection, or via some other network (such as the Internet or a closed local network such as an Intranet). The collection of computing devices may collectively communicate with other computing devices over the network 110. Mining node 120d is shown as a collection of dedicated processors and storage devices.

The skilled person would thus appreciate that a mining node 120 is any apparatus suitable for performing a mining method such as those described herein. For example, a mining node 120 may comprise one or more computing devices such as laptop computers, desktop computers, workstations, personal digital assistants, blade servers, mainframes and so on.

Each mining node 120 is configured to communicate with at least one other mining node 120 and optionally other devices over the communication network 110 to form a peer-to-peer blockchain network 115 of devices that take part in the sharing, storing and/or establishment of a blockchain. Although the blockchain network 115 of FIG. 1A is shown as comprising only the mining nodes 120, the blockchain network 115 may further comprise one or more authority servers 130 (although only one authority server 130 is shown in FIG. 1A), for example if versions of the blockchain are sent to the authority server for storage, or if the authority server itself is configured to function also as a mining node.

Each mining node 120 is further configured to communicate with one or more authority servers 130 (although only a single authority server 130 has been shown in FIG. 1A) over a communication network 110. While FIG. 1A shows the authority server 130 communicatively coupled with the same communication network 110 as the mining nodes 120, this need not be the case. Furthermore, although one authority server 130 is shown in FIG. 1A, there may be further authority servers 130. In some examples, an authority server 130 may also be configured to operate as a mining node 120, although in such examples, the authority server 130 may be required to seek a signed token for any new block record from at least one other authority server 130.

An authority server 130 may comprise any suitable computing apparatus, such as the computing apparatus 200 shown in FIG. 2 and discussed below. An authority server 130 is a computing device trustable by several mining nodes 120, such that a digital signature or other form of verifiable authorisation (such as a certificate) issued by the authority server 130 can enable a mining node to determine that an operation, or some sort of data signed by the authority server 130, has been marked as valid and is therefore trustable by the mining node 120. Each authority server 130 is configured to communicate with one or more of the mining nodes 120 over a communications network 110, to communicate with one or more data sources 150, and in the example of FIG. 1A to communicate with a central authority server 140 also. An authority server 130 may be operated by, for example, a trusted research institute or public body. A data source 150 is any suitable repository of information, such as a database, that can provide data to an authority server 130 for processing as part of a data package by a mining node 120. A data source 150 is therefore configured to communicate with/be read by an authority server 130 so as to provide one or more pre-processed data items to the authority server 130. The authority server may accordingly generate or create or collate multiple data packages for distribution to mining nodes 120.

The skilled person would appreciate that the term "data source" should be interpreted broadly and may comprise the physical hardware/server etc. from which the data items are retrieved.

Communication system 100 may also comprise a central authority server 140. The central authority server 140 is configured to track and validate the authority servers 130 such that the authority servers 130 are trustable by the relevant mining nodes 120. For example, the central authority 140 may assign signed certificates to each authority server 130. The certificates may be used by the authority servers 130 in signing a token to act as proof-of-work. The mining nodes 120 may check whether a block record of a blockchain is valid by checking first the validity of an authority server 130 that issues a signed token, and by checking the signed token itself.

The central authority 140 may itself comprise a data source 150. That is, the central authority 140 may collate data items and distribute those data items to the authority servers 130 for processing prior to their onward transmission to mining nodes 120. The authority servers 130, on receiving data outputs from the one or more mining nodes 120, may communicate verified data outputs to the central authority 140.

The skilled person would appreciate that the central authority 140 may or may not be present, and in some embodiments is not required. For example, in some private blockchain implementations, there may be a single authority server 120 and no requirement for a further authority (central authority).

Figure 1B:
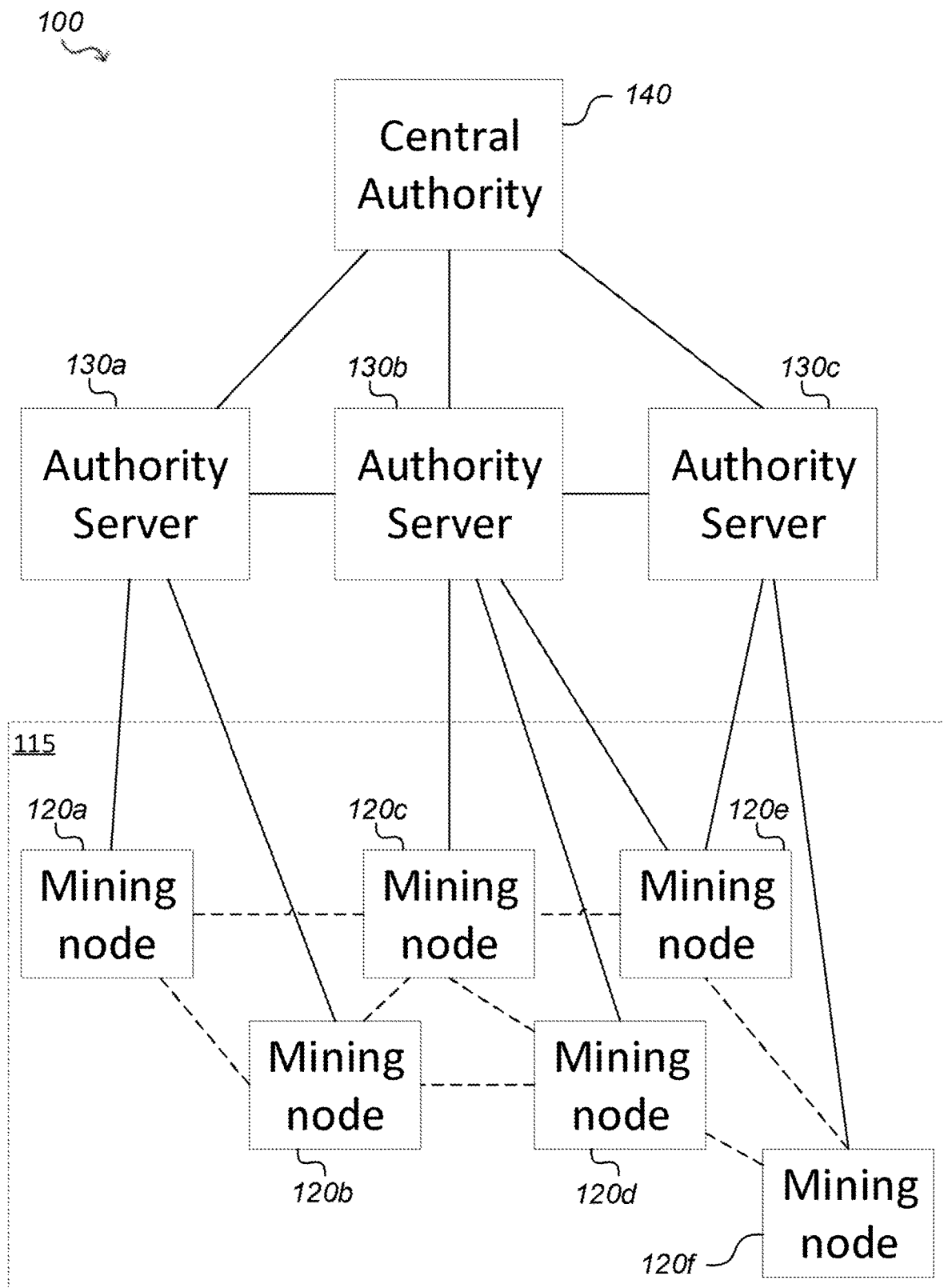
FIG. 1B shows interaction relationships between several parties described in relation to FIG. 1A.

FIG. 1B illustrates a hierarchical structure such as that used by entities of FIG. 1A. The skilled person would appreciate that FIG. 1B is for illustrative purposes only and that alternative communication structures are possible. The central authority 140 is able to certify each of the authority servers 130*a*, 130*b* and 130*c* such that they may be trustable by relevant mining nodes and by each other to inject or feed in data packages to be processed by the mining nodes, and may upon verification of results of a data package sign a token to be used as proof-of-work in a block record of a blockchain.

In FIG. 1B, first authority server 130*a* is shown communicatively coupled to first mining node 120*a* and second mining node 120*b*, second authority server 130*b* is shown communicatively coupled to third mining node 120*c*, fourth mining node 120*d* and fifth mining node 120*e*, and third authority server 130*c* is shown communicatively coupled to fifth mining node 120*e* and sixth mining node 120*f*. The skilled person would appreciate that further or fewer authority servers 130 may be included and further mining nodes may be included.

The mining nodes 120*a*, 120*b*, 120*c*, 120*d*, 120*e* and 120*f* may be communicatively coupled on a mining node network/blockchain network 115 (illustrated by the dashed lines between the mining nodes). That is, the mining nodes 120 may communicate a copy of a blockchain or a block record for a blockchain to other mining nodes 120. In some embodiments, one or more of the authority servers 130 may form part of the blockchain network such that they are enabled to receive or transmit copies of a blockchain to mining nodes 120 (or to other authority servers 130). However, in FIG. 1B this is not illustrated. In FIG. 1B, the authority servers 130 are outside of the blockchain network (that is, they do not send or receive copies of the blockchain) but feed in data packages to be processed by mining nodes 120 and validate results of processing of data packages by the mining nodes 120.

In an example, first authority server 130*a*, after being certified by a central authority 140, may receive multiple pre-processed data items from multiple data sources (150, FIG. 1A), parcel several data items into data packages and issue a data package to each of mining nodes 120*a* and 120*b* to be processed. Each data package contains a plurality of datasets, and each of the plurality of datasets comprises signal information. While no data packages are identical, the datasets may be comprised within multiple data packages. Furthermore, first authority server 120*a* may store metadata concerning which data items are in which data package, such that when results of the processing of the data package are verified, the processed results may be communicated back to a relevant user/data source 150. First authority server 130*a* may further remove identifying features concerning the source of the data item or the subject to which the data item pertains, and to instead include some systematic identifying information of the datasets in the data packages in order to avoid sending personal information to a mining node. In this way, data privacy is increased as no mining node may feasibly determine to which subject, problem or issue a particular dataset relates.

Data packages may contain further information such as parameters to be used by the mining nodes in evaluating the datasets.

Each mining node 120 is configured to attempt to add a block record to a blockchain, using a signed token from an authority server 130 as verifiable evidence of work undertaken. Accordingly, first mining node 120*a* processes the data package from first authority server 130*a* to convert the signal information of each dataset to a corresponding data output, and communicates the plurality of data outputs to the first authority server 130*a* for verification.

First authority server 130*a* may receive data outputs from first mining node 120*a*, second mining node 120*b* and further mining nodes (not shown) of the blockchain network 115. The first authority server 130*a* can verify a data package received from first mining node 120*a* by checking that a data output for each given dataset of the data package provided to first mining node 120*a* substantially matches (within error bounds) data outputs provided for that given dataset provided by other mining nodes (e.g. second mining node 120*b*). Once the first authority server 130*a* has determined that the results of the data package from the first mining node 120*a* are verified, the first authority server 130*a* sends a signed token to the first mining node 120*a* for use in appending a block record to a blockchain. The first authority server 130*a* can, after consulting the stored metadata, send the results of the data processing by the mining nodes 120 to the data sources or other rightful stakeholders.

First mining node 120a, on receiving a signed token from the first authority server 130a, can use the signed token as proof-of-work to append a block to a blockchain, and to then communicate that block to the wider blockchain network 115. In FIG. 1B, first mining node 120a is shown connected to second mining node 120b and third mining node 120c; first mining node 120a may therefore communicate the created block via peer-to-peer communication with second mining node 120b and third mining node 120c.

The first authority server 130a may also be configured to coordinate a payment of a cryptocurrency to the mining node 120a upon verification of the results from the first mining node 120a. Advantageously, such a payment may provide incentive for the first mining node 120a to undertake computationally intensive task of converting the datasets of the data package to data outputs and to thus take part in the upkeep of the blockchain.

After second mining node 120b receives a block from first mining node 120a, the third mining node 120c may check that the block is valid. The third mining node 120c may check that the block contains a signed token from an authority server 130 such as authority server 130a. The third mining node 120c may check that the signed token contains an indication that the issuer of the signed token (first authority server 130a) has been validated by the central authority 140. For example, the third mining node 120c may check via a communication with the second authority server 130b. The third mining node 120c may further check that the resultant blockchain of which the new block record from first mining node 120a is purportedly a part, is longer than a present blockchain stored locally at the third mining node 120c. If the third mining node 120c determines that the block record from first mining node 120a is valid, then the third mining node 120c communicates that block to other mining nodes (e.g. fourth mining node 120d and fifth mining node 120e). In this way, a valid block is adopted by consensus.

Figure 2:
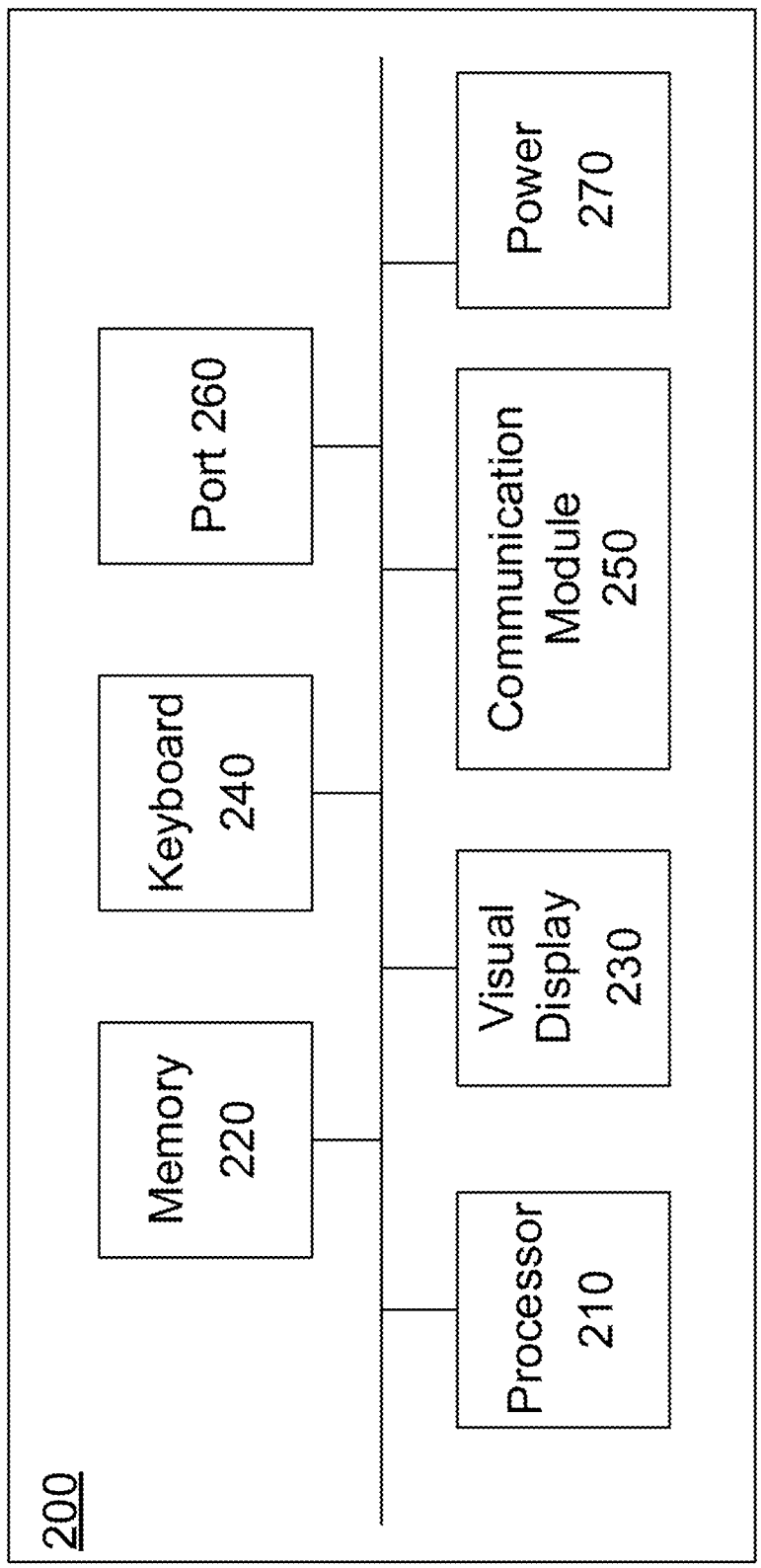
FIG. 2 shows a block diagram of computing apparatus.

FIG. 2 is a block diagram of a computing apparatus 200. For example, computing apparatus 200 may comprise a computing device, a server, a mobile or portable computer or telephone and so on. Computing apparatus 200 may be distributed across multiple connected devices. Computing apparatus 200 may be suitable for use as a mining node 120, an authority server 130, or a central authority 140. Other architectures to that shown in FIG. 2 may be used as will be appreciated by the skilled person.

Referring to the figure, computing apparatus 200 includes one or more processors 210, one or more memories 220, a number of optional user interfaces such as visual display 230 and virtual or physical keyboard 240, a communications module 250, and optionally a port 260 and optionally a power source 270. Each of components 210, 220, 230, 240, 250, 260, and 270 are interconnected using various busses. Processor 210 can process instructions for execution within the computing apparatus 200, including instructions stored in memory 220, received via communications module 250, or via port 260.

Memory 220 is for storing data within computing apparatus 200. The one or more memories 220 may include a volatile memory unit or units. The one or more memories may include a non-volatile memory unit or units. The one or more memories 220 may also be another form of computer-readable medium, such as a magnetic or optical disk. One or more memories 220 may provide mass storage for the computing apparatus 200. Instructions for performing a method as described herein may be stored within the one or more memories 220.

The apparatus 200 includes a number of user interfaces including visualising means such as a visual display 230 and a virtual or dedicated user input device such as keyboard 240.

The communications module 250 is suitable for sending and receiving communications between processor 210 and remote systems. For example, communications module 250 may be used to send and receive communications via a communication network 110 such as the Internet.

The port 260 is suitable for receiving, for example, a non-transitory computer readable medium containing one or more instructions to be processed by the processor 210.

The processor 210 is configured to receive data, access the memory 220, and to act upon instructions received either from said memory 220 or a computer-readable storage medium connected to port 260, from communications module 250 or from user input device 240.

A mining node 120 may comprise computing apparatus 200, or several such apparatuses. As explained above in relation to FIG. 1A, a mining node may comprise a single computing device or a small cluster of computing devices. As an example, first mining node 120a may comprise computing apparatus 200, the processor 210 may request a data package from the first authority server 130a (via communications module 250). Computing apparatus 200 may receive a data package from the first authority server 130a via communications module 250. The processor 210 may follow instructions stored in one or more memories 220 to analyse the received data package to convert the signal information of each dataset to a corresponding data output. The processor 210 may then communicate the plurality of data outputs to the first authority server 130a, the plurality of data outputs for use in establishing a proof-of-work for appending a block record to the blockchain. The computing apparatus 200 may receive a signed token from the first authority server 130a. The processor 210 may consult a current version of a blockchain stored in the one or more memories 220 to extract a unique identifier of the preceding block of the blockchain, and may retrieve payload data from a data pool of unprocessed payload data. The processor 210 may create a block record for the blockchain including the payload data, the unique identifier and the signed token from first authority server 130a. Using communication module 250, the new block may then be communicated to further mining nodes of the blockchain network 115, such as second mining node 120b and third mining node 120c. The new block may be communicated on its own or the entire blockchain including the new block may be communicated. Furthermore, a mining node 120a comprising computing apparatus 200 may receive a purported block from another mining node 120, such as third mining node 120c. The processor 210 may then check that the block comprises a signed token from an authority server (and may consult a database of trusted authority servers stored in the memory 220 or communicate with the first authority server 130a to verify the source of the signed token). The processor may make other additional checks of the purported block. The processor 210 may then determine that the new block is valid and store an updated version of the blockchain in memory 220, or may disregard the new block.

In some embodiments an authority server 130 such as first authority server 130a may comprise computing apparatus 200. In such embodiments, the communications module 250 may receive multiple pre-processed data items from multiple data sources 150. The processor 210 may divide the multiple pre-processed data items into independently processable datasets, package a selection of the independently processable datasets into a data package, and store metadata in one or more memories 220 concerning which independently processable datasets are included in the data package. Information that can identify users (e.g. a subject to which a data item relates) may be stored as metadata, and datasets of data packages may be tracked using systematic identifiers instead. The data package may then be communicated to a mining node 120 such as first mining node 120a. The computing apparatus 200 may receive information containing a first plurality of data outputs from the first mining node 120a of the network, each data output of the first plurality of data outputs determines from the first data package analysed by the first mining node 120a. The computing apparatus 200 may receive further data outputs from other mining nodes (such as second mining node 120b). The processor 210 may verify the first plurality of data outputs by comparing the first plurality of data outputs with the stored one or more further pluralities of data outputs. In response to verifying the first plurality of data outputs, the processor 210 may cryptographically sign a token including details identifying the first mining node 120a, a timestamp, and a hash of the first data package, and may communicate the signed token to the first mining node 120a. The verified data outputs may be communicated to the data sources 250, to the central authority 240, or to other rightful destinations. For example, a user to which a data item relates may be sent an email providing a link to a website from which their processed results can be downloaded securely.

The skilled person would appreciate that other architectures to that shown in FIG. 2 may be used. The skilled person would further appreciate that apparatus such as computing apparatus 200 may be comprised in a central authority 240 and/or in a data source 250.

Figure 3:
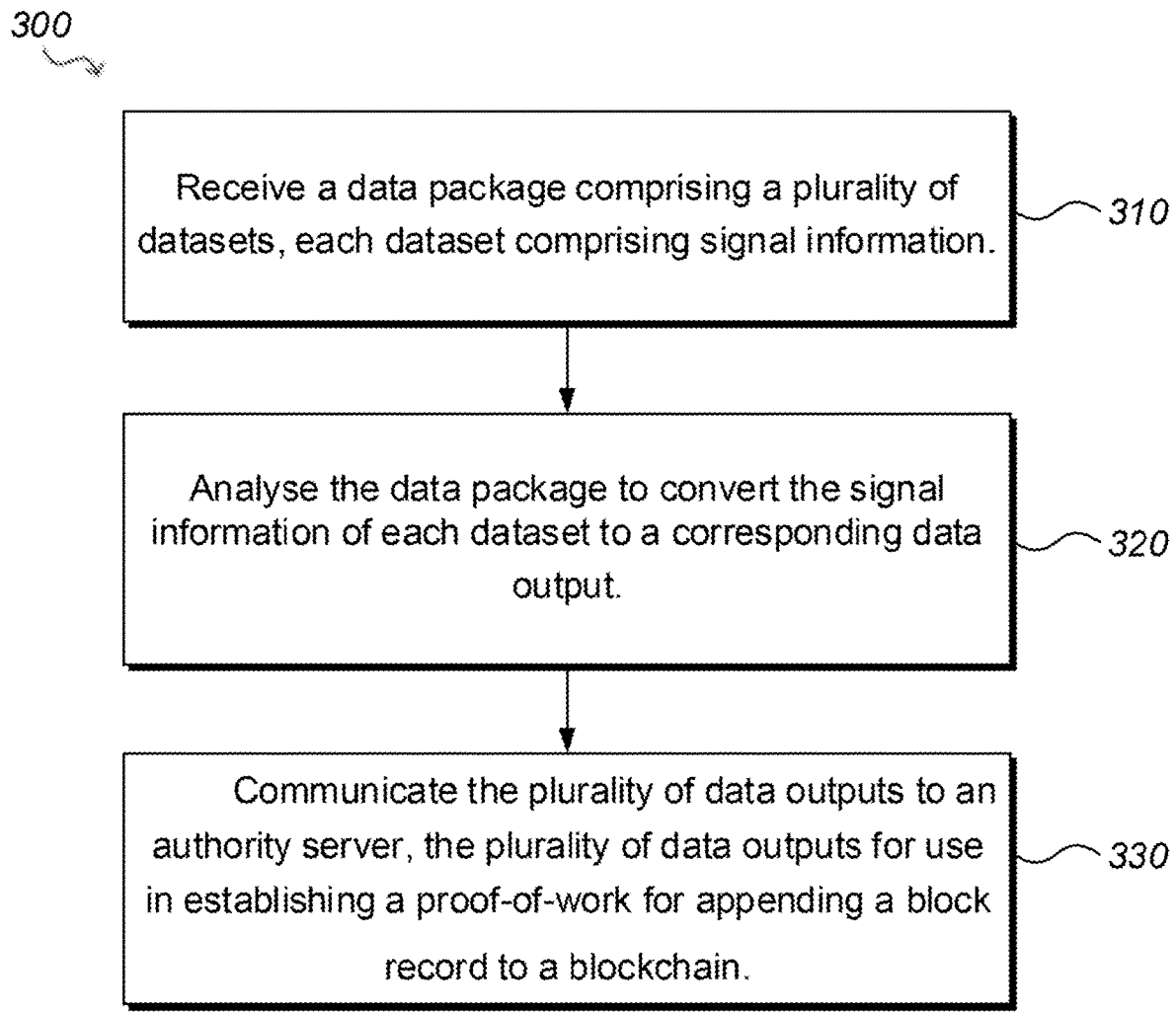
FIG. 3 shows a flowchart.

FIG. 3 is a flowchart of a method 300 for performance by computing apparatus such as computing apparatus 200. The method is suitable for performance by a mining node 120. The method is suitable for appending a block record to a blockchain stored on mining nodes of a blockchain network 115.

At 310, a data package is received. The data package comprises a plurality of datasets, each dataset comprising signal information.

The signal information may be any suitable information signal. As an example, the information signal may comprise raw data produced by a nanopore sequencer, the raw data indicative of a polynucleotide sequence. Each dataset may relate to a different subject. For example, a first dataset of the data package may relate to a first human subject, a second dataset of the data package may relate to a second human subject, a third dataset of the data package may relate to a plant and so on.

At 320, the data package is analysed to convert the signal information of each dataset to a corresponding data output. For example, converting the signal information of each dataset may comprise converting one data type to another. The analysis may be a form of "base calling", in which the signal information is converted into a polynucleotide sequence such as a DNA sequence or RNA sequence.

At 330, the plurality of data outputs is communicated to an authority server 130. The plurality of data outputs may be communicated to an authority server 130 in encrypted form. The plurality of data outputs is for use in establishing a proof-of-work for appending a block record to a blockchain.

Figure 4:
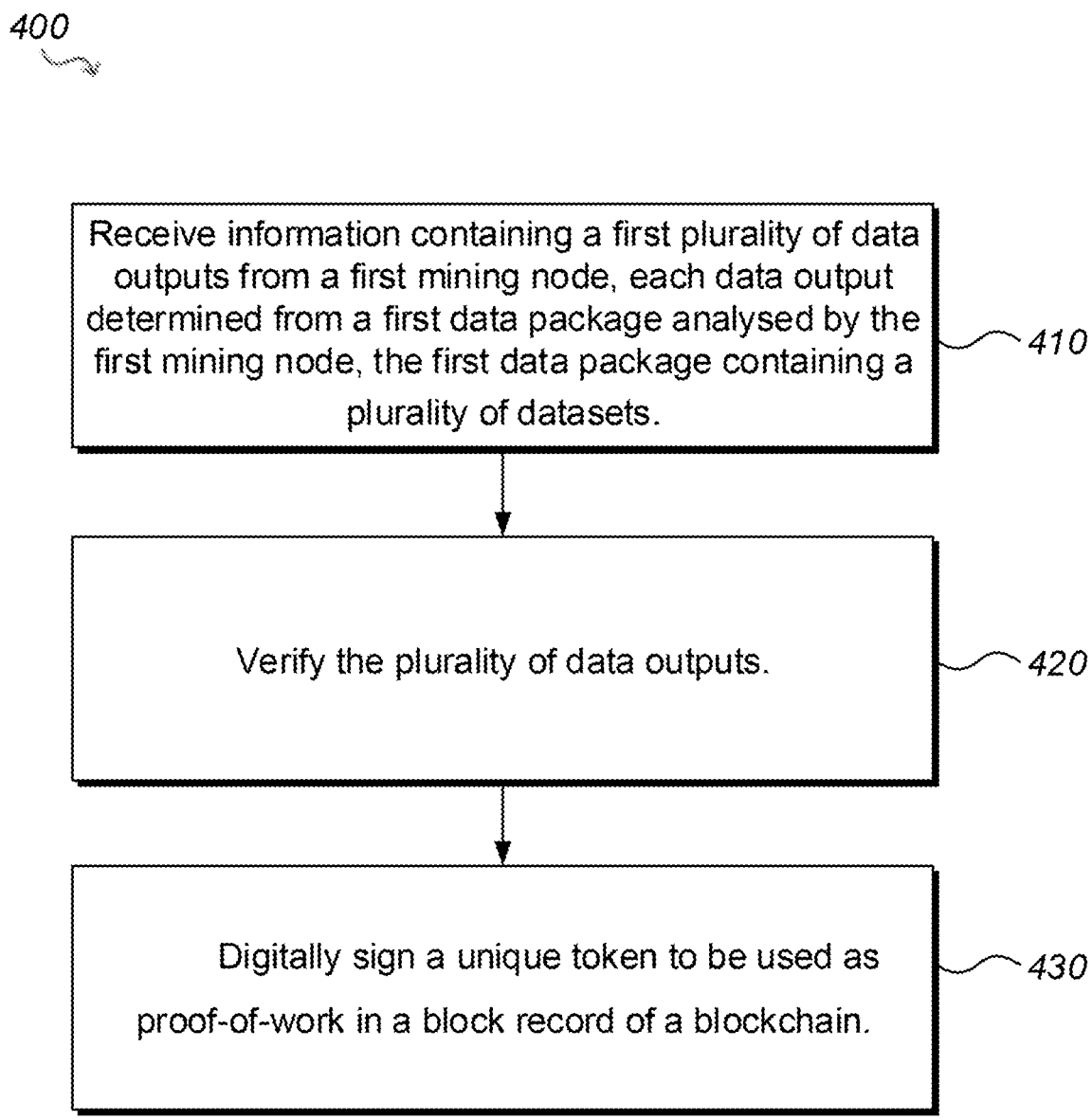
FIG. 4 shows a flowchart

FIG. 4 is a flowchart of a method 400 for performance by computing apparatus such as computing apparatus 200. The method is suitable for performance by an authority server 130.

At 410, information is received containing a first plurality of data outputs from a first mining node. Each data output has been determined from a first data package analysed by the first mining node, the first data package containing a plurality of datasets, each dataset comprising signal information.

At 420, the plurality of data outputs is verified. Verification of the data outputs may take any suitable form.

At 430, a unique token is digitally signed. The unique token is for use as proof-of-work in a block record of a blockchain.

Figure 5:
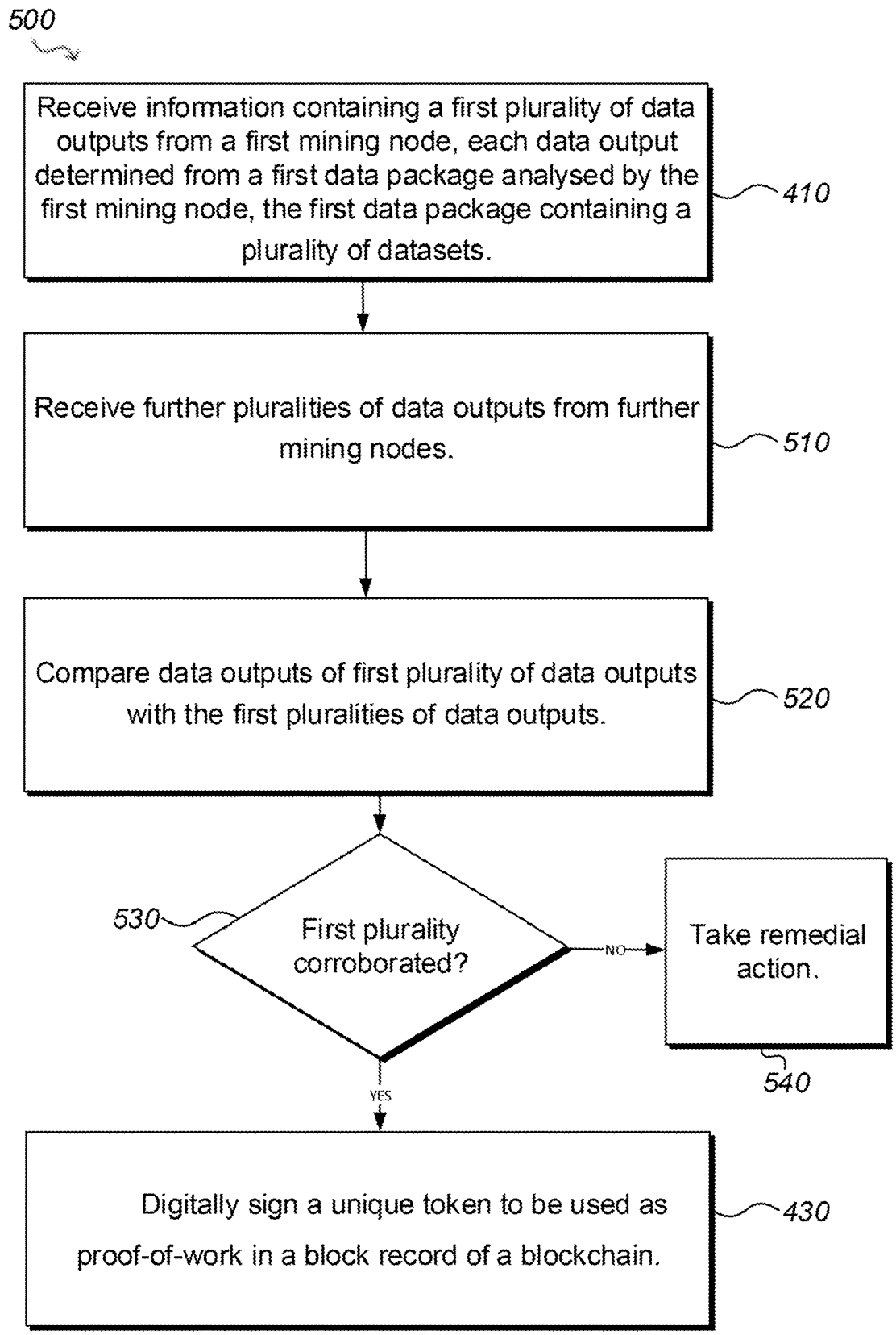
FIG. 5 shows a flowchart.

FIG. 5 shows a flowchart of a method 500 for performance by computing apparatus such as computing apparatus 200. FIG. 5 provides further details on a possible implementation of the verifying stage 420 of FIG. 4.

The method begins with step 410, described above in relation to FIG. 4, before proceeding to step 510.

At 510, further pluralities of data outputs are received from further mining nodes. As each mining node 120 processes a different data package, no two pluralities of received data outputs will be the same. However, if the data packages contain overlapping datasets, then the data outputs from the first mining node 120a can be compared with the data outputs received from several other mining nodes. The skilled person would appreciate that the further data outputs may be received prior to, subsequent to, or simultaneous to step 410. At 520, data outputs of the first plurality of data outputs are compared with the further data outputs from the further mining nodes. In this way, each data output may be corroborated. Once a corroboration condition is met for each data output of the first plurality of data outputs, for example by a threshold number of different mining nodes 120 submitting substantially the same results for the same data output (and subject to any error conditions being satisfied), then the first plurality of data outputs may be considered verified.

For any given dataset (included in multiple data packages, each distributed to a different mining node 120), the corresponding data output received from any given mining node may contain errors. Such errors may creep in due to the noisiness of the signal information comprised within the dataset. For example, when the information signal comprises raw data from a nanopore sequencer, the different mining nodes running conversion algorithms for converting that raw data to sequence data may not identically interpret the information signal, leading to minor discrepancies between the data outputs received from different mining nodes. Accordingly, determining that each data output of the first plurality of data outputs has been corroborated within a predefined error threshold may comprise determining that a threshold number of mining nodes agree on a subunit of that data output, for example a nucleobase of a DNA sequence.

Accordingly, even though a received first plurality of data outputs may contain some minor errors, such errors are resolvable by a comparison with data outputs received from a suitable number of other mining nodes. The first plurality of data outputs may therefore be considered verified even if it is determined that there are some minor errors in the outputs.

At 530, a determination is made as to whether or not the first plurality of data outputs from the first mining node has been corroborated. If yes, then the method proceeds to step 430 (described above in relation to FIG. 4). If no, then remedial action is taken. Such remedial action may be simply disregarding the first plurality of data outputs, or may comprise logging identification information concerning the mining node. Remedial action may comprise storing the first plurality of data outputs for further comparison as further results from further mining nodes are received.

Figure 6:
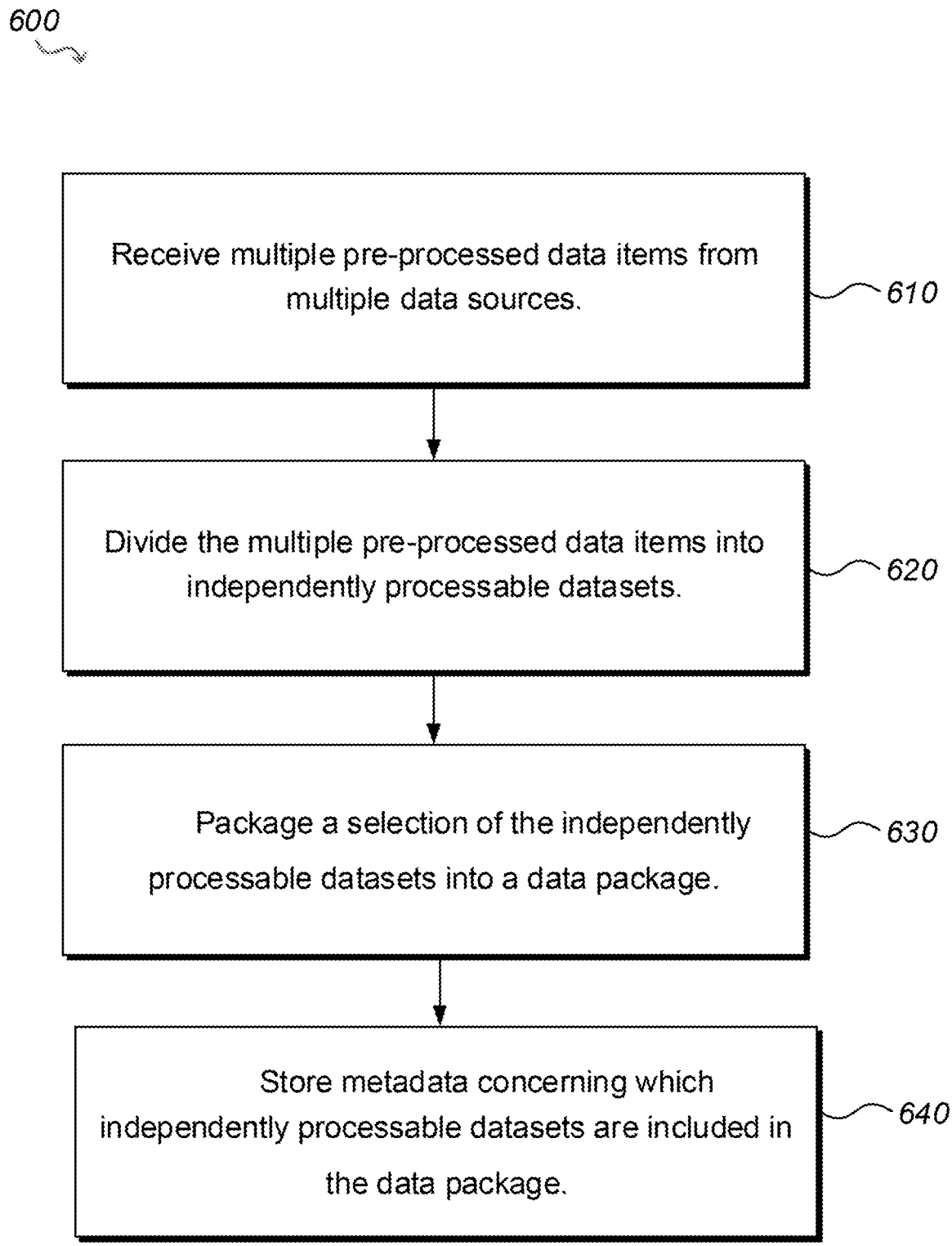
FIG. 6 shows a flowchart.

FIG. 6 shows a flowchart of a method 600 for performance by computing apparatus such a computing apparatus 200. The method may be performed by an authority server 130 and may be performed prior to step 410. At 610, multiple pre-processed data items from multiple data sources are received. Such data items may comprise, for example, large amounts of raw data produced from a nanopore sequencer. The raw data may comprise, for example, information concerning how current across a nanopore through which an analyte translocates varies over time. Data items may contain any problem that may be analysed by the computing power of a mining node. Each data item may contain for example, raw data representative of a DNA sequence for a corresponding subject. That is, a first data item may relate to a first subject, and second data item may relate to a second data subject and so on.

At 620, the multiple pre-processed data items are divided into independently processable datasets. By dividing each data item up, different parts of each data item may be analysed separately. Accordingly, it is infeasible for any mining node to retrieve full information concerning the original data item, as each mining node may only process one or a small few of datasets divided from a pre-processed data item out of possibly thousands of such datasets. When the data item contains, for example, raw data relating to a subject's DNA being sequenced by a nanopore sequence, it becomes infeasible for any mining node to collate enough information concerning the data item to be able to reproduce either the entire raw data for that subject or the processed results of the entire raw data for that subject (in this example, the full DNA sequence of that subject). Accordingly, dividing up the data items in this way helps to ensure that data privacy in maintained.

At 630, a selection of the independently processable datasets are packaged into a data package. For example a dataset indicative of a portion of a DNA sequence of a first subject may be included in the data package, a dataset indicative of a portion of a DNA sequence of a second subject may be included in the data package, and so on, such that the data package contains many independent datasets relating to many subjects and possibly from many data sources 150.

At 640, metadata concerning which independently processable datasets are included in the data package is stored. In this way, once results are received subsequently from the mining nodes 120, it is possible to determine which results relate to which data items. Metadata may include, for example, an indication of the data source, and subject to which that data item relates, reference numbers/identifiers concerning the data items, reference numbers/identifiers concerning the data packages into which the data set is packaged, and so on. Metadata may comprise any data submitted by a user (for example, a submitter of nanopore sequencer signal information for processing) which is not required for transformation of the data. This may include, for example, the date and time that the sequencing run took place, the identity/identities of the submitting user/users, and/or the identity of the samples that were sequenced.

Figure 7:
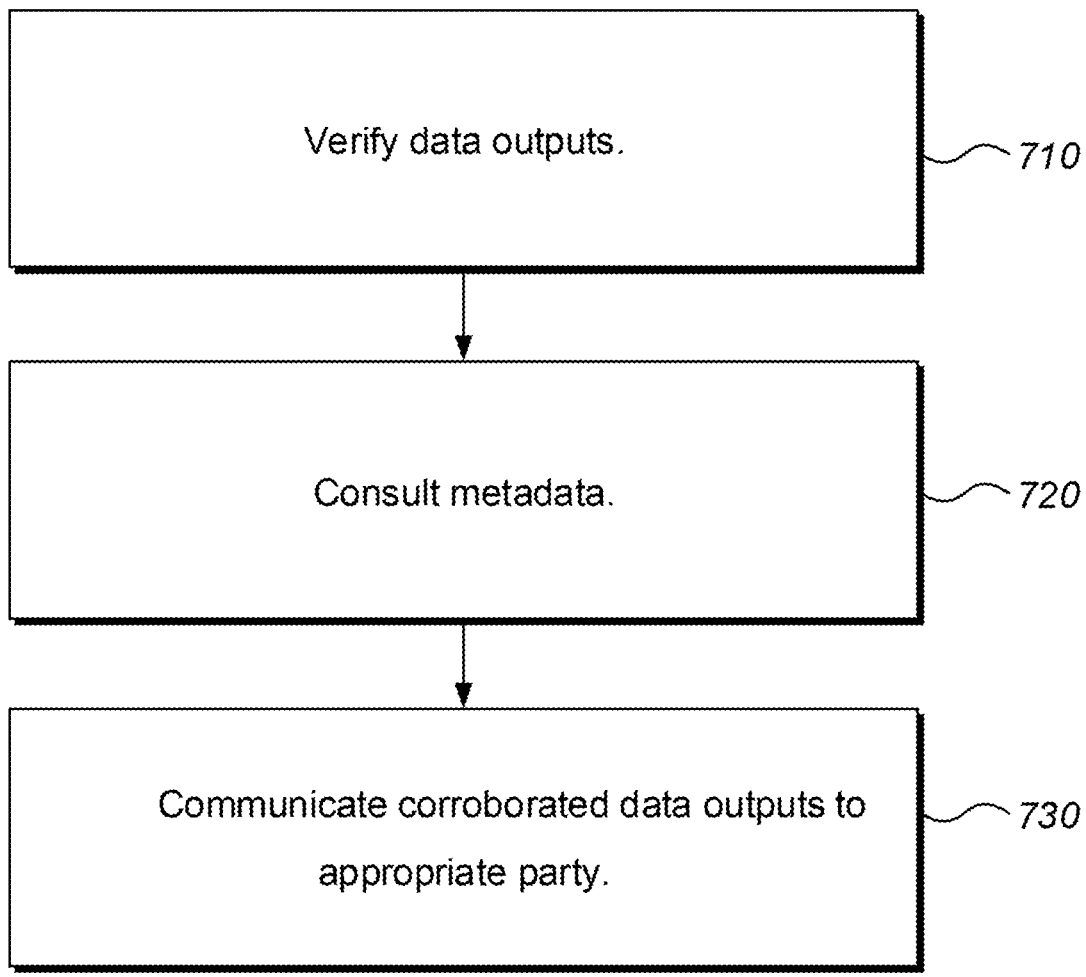
FIG. 7 shows a flowchart.

FIG. 7 shows a flowchart of a method 700 for performance by computing apparatus such as computing apparatus 200. The method is suitable for processing by an authority server 130.

At 710, data outputs are verified. This step may correspond to step 420 of FIG. 4. Some form of error correction may be performed on the data outputs if it is determined that there are minor discrepancies between data outputs received from different mining nodes. In this way, error corrected data outputs may be returned to rightful recipients.

At 720, the stored metadata is consulted. The stored metadata is consulted in order to determine to which original data item and data source a verified data output relates. The metadata may be amended to denote that a given dataset has been corroborated. The metadata may be amended to denote that a given data item has been fully converted by mining nodes into a selection of (error-corrected) corroborated data outputs.

At 730, corroborated data outputs are communicated to the appropriate party. This may be the data source 150 from which the data item originated, or may be a central authority 140 or some other device.

Figure 8:
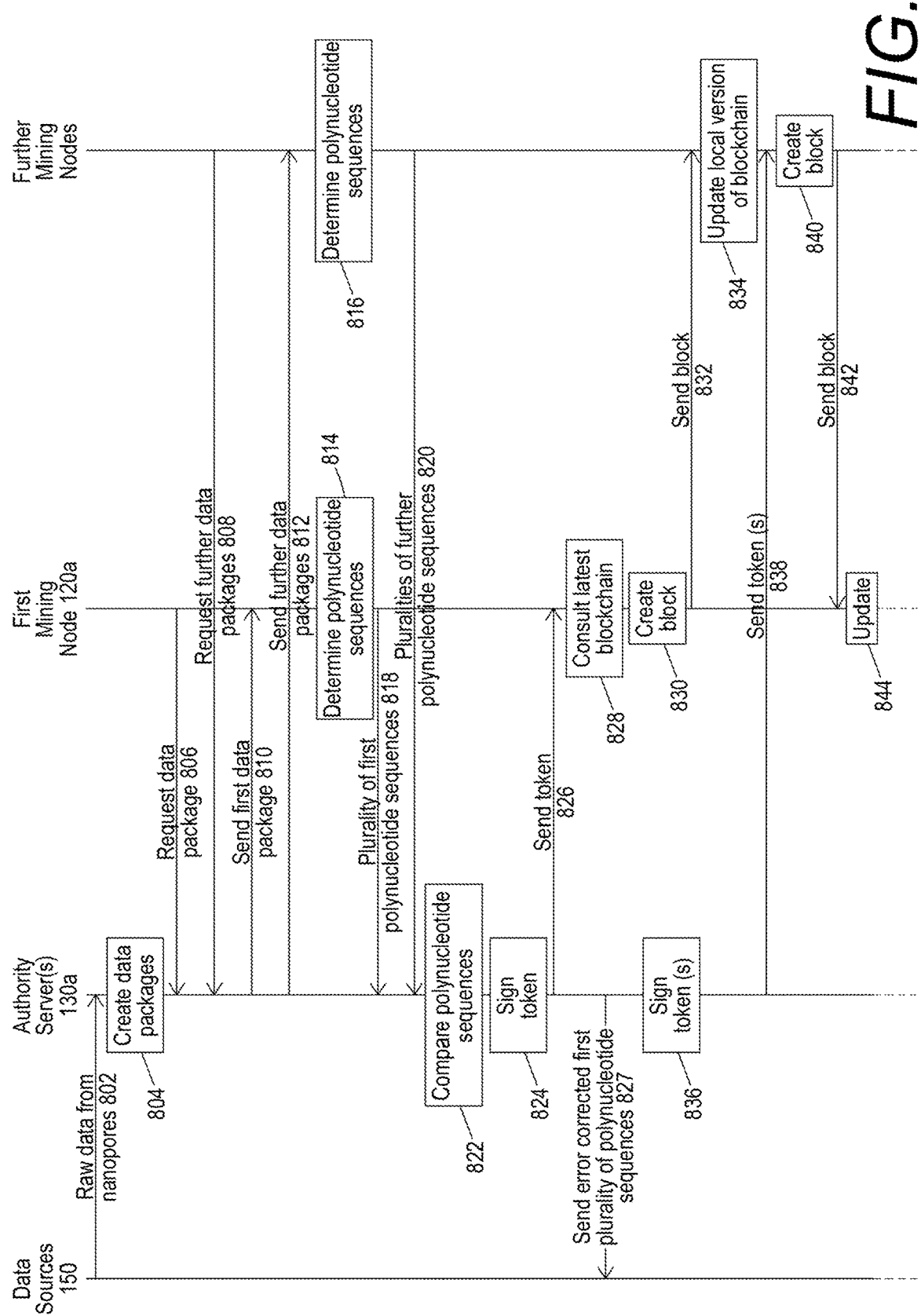
FIG. 8 shows a sequence of events according to an example whereby a block is appended to a blockchain.

A description of an example of a processing task involving mining nodes 120 and authority servers 130 will now be described in relation to FIG. 8. In the example of FIG. 8, the work to be undertaken by a mining node involves base calling, a process by which current information (possibly from a nanopore sequencer) is converted into a polynucleotide sequence.

At step 802, a data source 150 communicates data items containing raw data from nanopore sequencers to an authority server 130. Each data item relates to a different subject, such that a first data item relates to a DNA sequence of a first person, a second data item relates to an RNA sequence for a second person, a third data item relates to a DNA sequence of a third person, a fourth data item relates to a DNA sequence for a plant and so on. Each data item thus concerns a different polynucleotide sequence.

At 804, an authority server 130a creates a plurality of data packages. The authority server 130a divides up each of the received data items into a collection of datasets that may be processed independently. A selection of datasets may then be collated into a data package, each dataset of a data package originating from a different data item (that is, each dataset of a data package relating to a different polynucleotide sequence). In creating the data packages, the authority server 130a may additionally include a number of decoy datasets in the data packages, for which the results of processing of the decoy datasets is known. Such decoy datasets may be used to help verify results received from mining nodes—if a received results package does not include the correctly processed results of the decoy datasets, then the mining node from which the results package originated may have attempted to cheat.

At 806, a first mining node 120a requests a data package from the authority server 130a. At 808 further mining nodes (such as second mining node 120b and so on) request further data packages from the authority server 130a. Of course, the order of steps 806 and 808 may be reversed or occur substantially simultaneously.

In response to the requests, the authority server 130a sends a first data package to the first mining node 120a and sends further data packages to the further mining nodes.

At 814, the first mining node 120 processes the signal information provided in the first data package in order to determine the polynucleotide sequence portions to which each dataset relates. Similarly, at 816, the further mining nodes each process their respective further data packages to determine polynucleotide sequences.

The first plurality of polynucleotide sequences determined by the first mining node 120a is sent (818) to the authority server 130a. Similarly, the further pluralities of polynucleotide sequences determined by the further mining nodes 120 are sent (820) to the authority server.

After receiving the first plurality of polynucleotide sequences and the further plurality of polynucleotide sequences, the authority server 130a compares (822) the different polynucleotide sequences. The skilled person would appreciate that the authority server 130a is likely to receive results from different mining nodes at different times, and so the comparison is an ongoing process every time new results packages are received. As described above, each polynucleotide sequence of the first plurality of polynucleotide sequences is checked against relevant polynucleotide sequences received from other mining nodes for the same initial dataset. Furthermore, the authority server 130a may check that any results of processing of decoy datasets correspond to predetermined results stored in memory at the authority server 130a.

If a determination is made that the first plurality of polynucleotide sequences has been verified (by finding substantially the same results as other mining nodes), then the authority server 130a signs (824) a token. For example, the authority server 130a may digitally sign some identifier including a hash of the first data package sent to the first mining node, the identity of the first mining node, a timestamp, and any other relevant data. The token is then sent (826) to the first mining node 120a. The token may further comprise some information encrypted with a public key of the first mining node 120a such that only the first mining node 120a can decrypt the information using a corresponding private key of a public-private key pair. In this way, the authority server 130a may ensure that only the first mining node 120a can use the signed token as evidence of work performed in converting the first data package to a first plurality of polynucleotide sequences.

The authority server 130a may additionally cause a payment of a digital currency or cryptocurrency to be paid to the first mining node 120a upon verification of the first plurality of polynucleotide sequences. For example, the signed token may contain some information which, when processed as part of the blockchain protocol, releases some cryptocurrency to the first mining node 120a.

The authority server then sends (827) the (error-corrected) first plurality of processed polynucleotide sequences to the relevant data sources 150 as required. The skilled person would appreciate that the authority server 130a may send the processed data outputs as soon as they are verified, or once all datasets relating to an original data item have been processed and verified.

The first mining node consults (828) in memory the most recent version of the blockchain and creates (830) a new block record using at least the unique identifier of the preceding block of the blockchain, payload data, and the signed token. The first mining node 120a then sends (832) the block to the wider blockchain network including at least a second mining node 120b. Each mining node checks the validity of the block including checking for a valid signed token from an authority server such as authority server 130a. Once validated, a locally stored version of the blockchain is updated (834) to include the new block. In this way, the blockchain is updated at each mining node of the blockchain network.

The authority server 130a continues to process all results received from mining nodes. Once a second plurality of polynucleotide sequences from a second mining node 120b has been verified by the authority server 130a, the authority server signs (836) a second signed token and sends (838) the token to the second mining node 120b which creates (840) a new block record, and sends directly or indirectly the updated block record to other mining nodes including the first mining node 120a. The first mining node 120a then updates its own locally stored copy of the blockchain to include the new block from the second mining node 120b after validating the new block.

In this way, a base calling process can be used as a proof-of-work protocol for a blockchain implementation.

The skilled person would appreciate that the example described above in relation to FIG. 8 is not the only way in which a block may be appended to a blockchain. For example, there may be more or fewer data sources. Data may be continuously received from a data source or may be received as discrete packages of computer data. Many other variations will become apparent to the skilled person on reading the present description.

Figure 9:
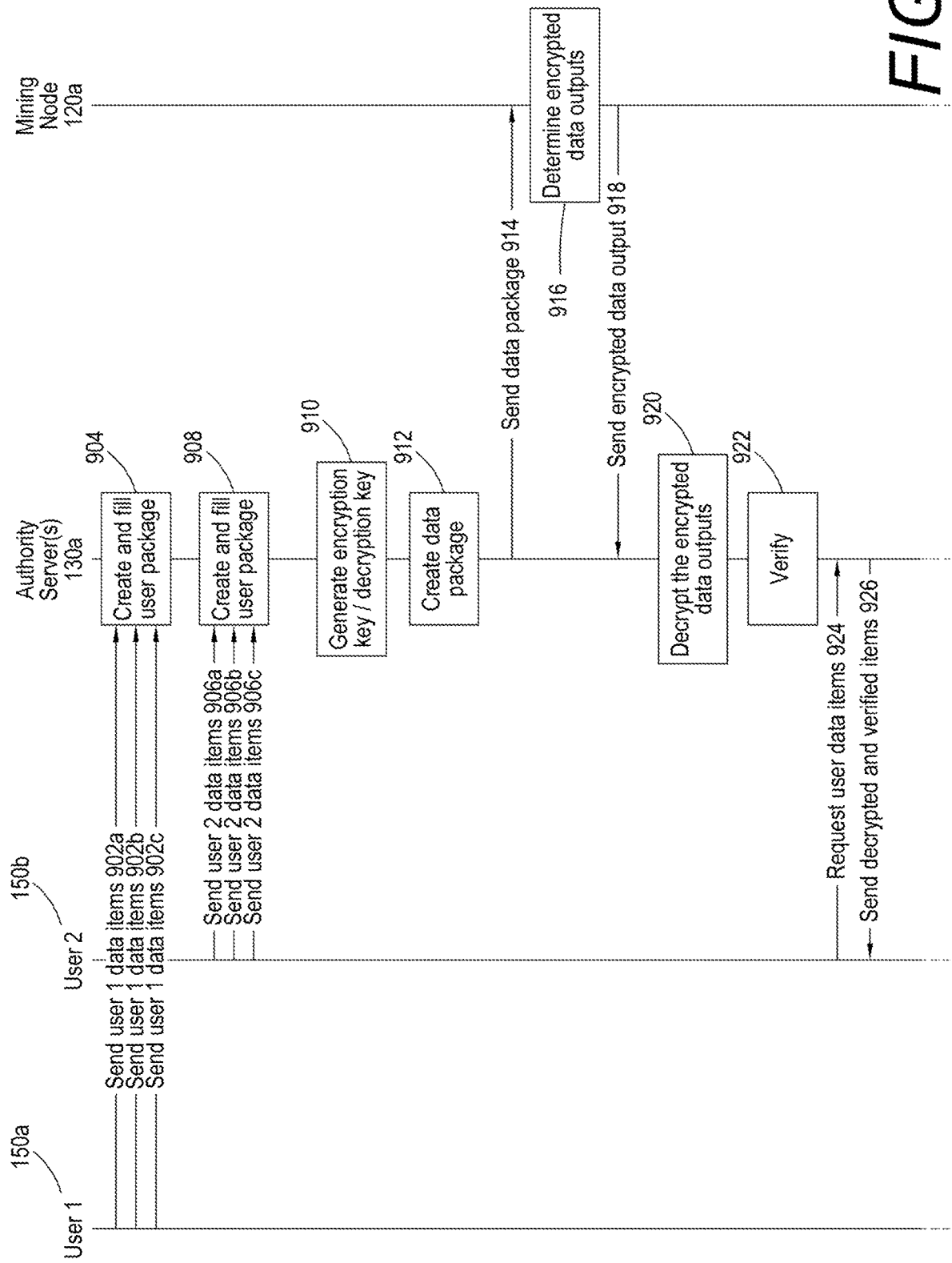
FIG. 9 shows a sequence of events according to another example.

In some scenarios, for example when a user desires a polynucleotide sequence such as DNA to be analysed, data privacy may be an important factor. A description of data submission and data retrieval by multiple different users to the authority server 130, and the encryption and decryption of data packages will now be provided in relation to FIG. 9. The skilled person would appreciate that the method described in FIG. 9 is compatible with the other methods described throughout this description (such as in FIG. 8).

As explained above, a data source 150 is to be interpreted broadly. Similarly, a user may be understood to mean any rightful stakeholder. For example, the user may be a laboratory researcher or medical personnel or a patient. The data source may be the user's computer and data items may be uploaded to an authority server 130 via e.g. a web portal, a file transfer service, or any other suitable means. The user may be a person in a lab uploading data items through a web application which provides the user several commands to allow interaction between the user and their uploaded data items. The data items uploaded by the user may comprise signal information (possibly from a nanopore sequencer) which is converted into a polynucleotide sequence by a mining node. The user may, as part of the data items or separately, also communicate other information to the authority server, such as a nanopore sequencer identifier indicating which nanopore sequencer generated a polynucleotide sequence.

At 902, user 1 (denoted as 150a in the figure, and taken to mean a data source operated by or on behalf of the user) communicates multiple data items 902a, 902b, and 902c to an authority server 130a. Although only three data items are shown, user 1 (150a) may communicate any number of data items to the authority server 130a, simultaneously or in a periodic manner. For example, a nanopore sequencer may take a long time to produce signal information indicative of a polynucleotide sequence and the user may communicate that signal information to the authority server 130a as a complete package once the sequencer has finished, or in multiple communications while the sequencer is running, or continuously while the sequencer is running. The authority server 130a creates a user package 904 to which data items from user 1 (150a) can be added. The authority server adds data items to user package 904 on behalf of user 1 until user package 904 is full. A "user package" here is understood to mean a collection of one or more data items—a user package may be full if, for example, a memory quota allocated to the user package is complete, or if an indication is received by the authority server 130a that there will be no further data received from user 1 in the near future.

At 906, a user 2 (denoted 150b) communicates multiple data items 906a, 906b, and 906c to an authority server 130a. Although only three data items are shown, user 2 (150b) may communicate any number of data items to the authority server 130*a*, simultaneously or in a periodic manner. The authority server 130*a* creates a user package 908 different to user package 904 to which data items from user 2 (150*b*) can be added. User 2 (150*b*) adds data items to user package 908 until user package 908 is full.

At 910, the authority server 130*a* generates one or more encryption keys and a corresponding decryption key.

At 912, the authority server creates a data package. The data package comprises a plurality of datasets and a corresponding plurality of encryption keys, each dataset comprising signal information. The signal information may be any suitable information signal. As an example, the information signal may comprise raw data produced by a nanopore sequencer, each nanopore sequencer associated with an identifier stored in the memory of the authority server, and the raw data indicative of a polynucleotide sequence. Each data package comprises datasets submitted by multiple different users (150). For example, a first dataset of the data package may relate to a first human subject, submitted by user 1 (150*a*). A second dataset of the data package may relate to a second human subject, submitted by user 2 (150*b*).

At 914, the authority server 130*a* sends a data package to a mining node 120*a* and may also send further data packages to the further mining nodes as described above in relation to step 810 of FIG. 8.

At 916, the mining node determines encrypted data outputs by using the distinct encryption key for each dataset within a data package to convert the signal information of each dataset to a corresponding encrypted data output. The mining node has computer-readable instructions stored in one or more memories 220 of the computing apparatus 200 to process a data package received from the authority server 130*a*. The computer readable instructions require an encryption key to process a data package received from the authority server 130*a*. Upon reception of the data package from the authority server 130*a*, the mining node uses the encryption key associated with each dataset to perform computer-readable instructions which convert the signal information of each dataset to a corresponding encrypted data output. Advantageously, data privacy is further enhanced. For example, in a situation in which a user has submitted signal information representative of a DNA sequence for processing, a mining node processing a dataset containing a small portion of that signal information by following locally stored instructions and using the received encryption key, would likely be unable to establish that the dataset represented a DNA sequence let alone establish the full DNA sequence for a given user.

The encrypted data output may be representative of an encoded polynucleotide sequence. The encoded polynucleotide sequence may be represented by a sequence of letters other than the usual uppercase IUPAC nucleotide code for the base, where the sequence of letters is determined from the encryption key. The encoded polynucleotide sequence may be represented by decoy features, such as inserting one or more random bases in a predictable pattern determined from the encryption key.

While above, the encryption has been described such that each dataset is converted to a corresponding encrypted data output, the skilled person would appreciate that further merging of the data outputs as part of the encryption process may occur, for example such that the encrypted data outputs are sent to the authority server as a composite unit of data. So long as the authority server 130*a* (or any other authority server to which the encrypted data outputs are communicated) has the required decryption key, any suitable form of encryption may be adopted. For example, an encryption key may direct the mining node processor to a look-up table stored in memory such that nucleotide bases are substituted for different characters without the mining node ever having access or knowledge of the decrypted base codes.

At step 918, the mining node sends the encrypted data outputs to the authority server 130*a*.

At step 920, the authority server receives the encrypted data outputs and uses the decryption key generated at 910 to decrypt the encrypted data. The decrypted data outputs may comprise sections of polynucleotide sequences. Decrypting the encrypted data may comprise using the decryption key to substitute the sequence of letters inserted at 916 for IUPAC nucleotide codes. In another example, decrypting the encrypted data may comprise using the decryption key to remove decoy features inserted at 916.

At 922, the decrypted data is verified by comparing decrypted data received from a plurality of mining nodes. FIG. 9 does not show the verification steps, but as outlined in FIG. 8, once the data is processed by the mining node and received by the authority server 130*a*, the authority server 130*a* can verify (822), sign tokens (836), send tokens to mining nodes (838), and a block can be added to the blockchain (830).

At 924, user 2 (150*b*) requests the decrypted and verified data items from authority server 130*a*. User 2 (150*b*) may request any of the decrypted and verified data items 920*a*, 920*b*, and 920*c* from the authority server. For example, the users may have the option through a web application to continuously request the latest validated results for any of the data items within a user package as they become available.

At 926, the authority server sends the requested decrypted and verified data items to user 2 (150*b*). The skilled person would appreciate that any number of users can request decrypted and validated results from an authority server 130, and that an authority server 130 can send the requested decrypted and verified data items to any number of authorized users.

Figure 10:
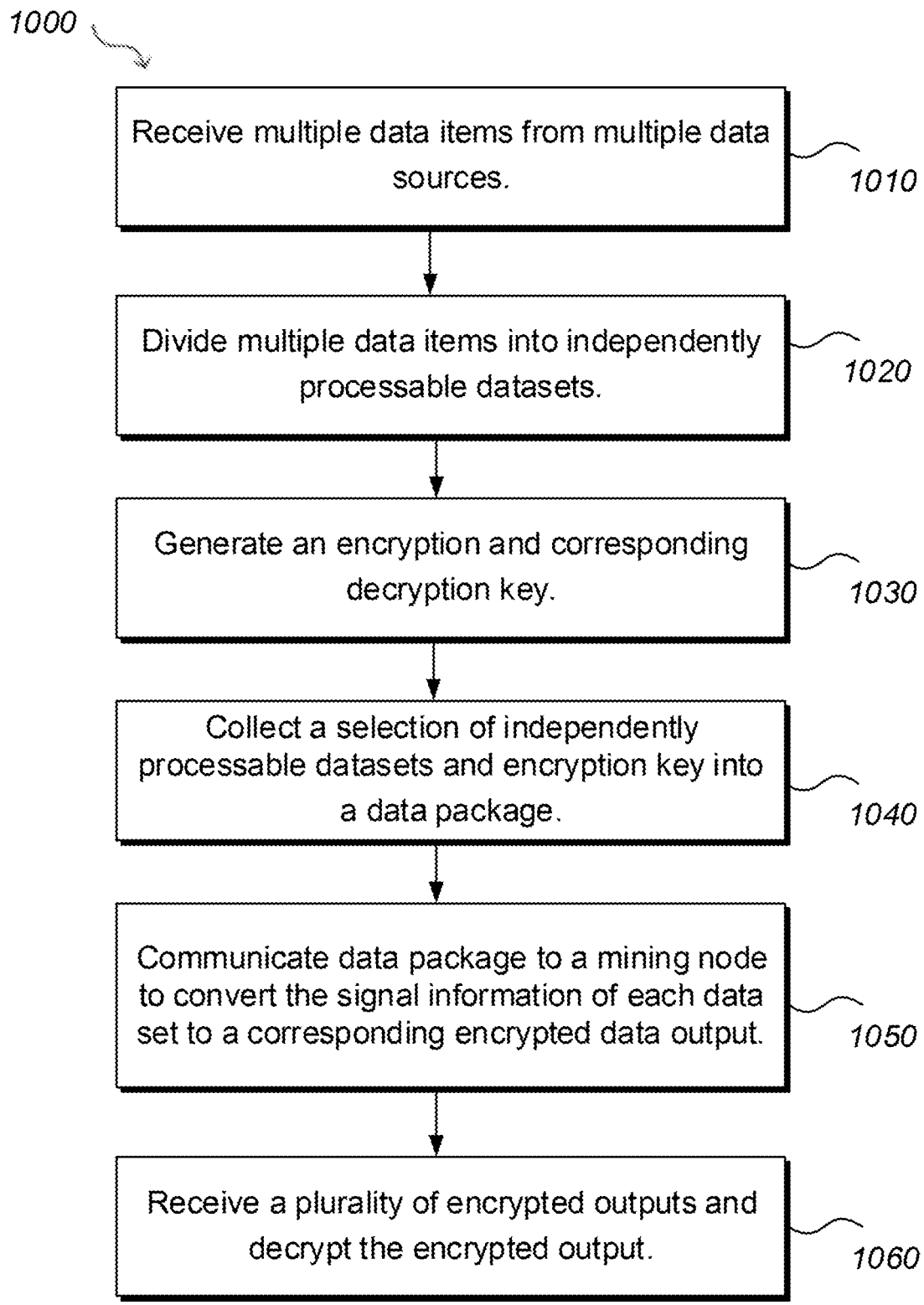
FIG. 10 shows a flowchart.

FIG. 10 is a flowchart of a method 1000 for performance by computing apparatus such as computing apparatus 200. The method is suitable for performance by an authority server 130*a*, or several authority servers in collaboration.

At 1010, multiple data items from multiple data sources 150 are received. Such data items may comprise, for example, large amounts of raw data produced from a nanopore sequencer. The raw data may comprise, for example, information concerning how current across a nanopore through which an analyte translocates varies over time. Data items may contain any problem that may be analysed by the computing power of a mining node. Each data item may contain for example, raw data representative of a DNA sequence for a corresponding subject. That is, a first data item may relate to a first subject, and second data item may relate to a second data subject and so on.

At 1020, the multiple data items are divided into independently processable datasets. By dividing each data item up, different parts of each item may be analysed separately.

At 1030, the authority server generates an encryption and a corresponding decryption key for each dataset within a data package. The encryption key is used by the mining node to encrypt the datasets of the data package. The skilled person would appreciate that an encryption key may be generated for use with the entire data package as opposed to for each individual dataset.

At 1040, the authority server 130 creates a data package. The data package in this example comprises a plurality of datasets and a corresponding plurality of encryption keys, each dataset comprising signal information.

At 1050, the authority server 130 communicates a data package to a mining node 120. The mining node 120 converts the signal information to a corresponding encrypted data output using the encryption key. Each mining node of this example has computer readable instructions stored in one or more memories 220 of the computing apparatus, which require an encryption key to process a dataset. The one or more processors 220 process the stored instructions using the encryption key to output encrypted data outputs. For example, when the datasets relate to a subject's DNA, the processor 210 processes the computer-readable instructions using the encryption key to output encoded polynucleotide sequences. The encoded polynucleotide sequences may be represented by a sequence of letters other than the usual uppercase IUPAC code for the base, where the sequence of letters is determined from the encryption key. The encoded polynucleotide sequence may be represented by decoy features, such as inserting one or more random bases in a predictable pattern determined from the encryption key. Accordingly, it becomes infeasible for any mining node to collate any information concerning the original data item, as the mining node is not privy to information relating to the original data item (such as knowledge that the data item represents a polynucleotide sequence). This advantageously leads to increased data privacy.

At 1060, the authority server 130 or another collaborating authority server with stored knowledge of the decryption key receives a plurality of encrypted data outputs from multiple mining nodes. The authority server 130 decrypts the encrypted output using the decryption key. The decrypted data outputs may comprise sections of polynucleotide sequences. Decrypting the encrypted data may comprise using the decryption key to substitute the sequence of letters inserted at 916 for IUPAC base codes. In another example, decrypting the encrypted data may comprise using the decryption key to remove decoy features inserted at 916.

The authority server may subsequently communicate the decrypted/deciphered data outputs to an authorized user.

Figure 11:
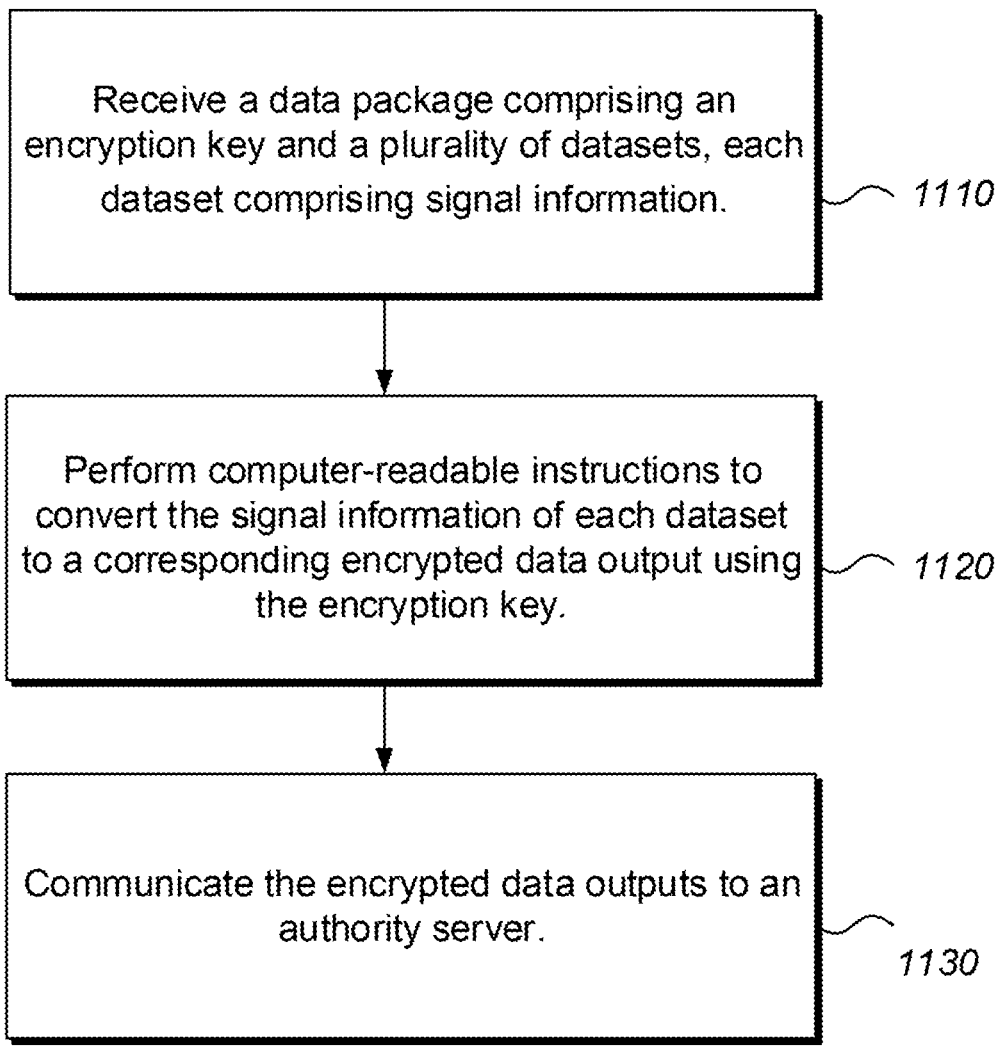
FIG. 11 shows a flowchart.

FIG. 11 is a flowchart of a method 1110 for performance by computing apparatus such as computing apparatus 200. The method is suitable for performance by a mining node 120. The method is suitable for appending a block record to a blockchain stored on mining nodes of a blockchain network 115.

At 1110, a data package is received from an authority server 130*a*. The data package comprises a plurality of datasets and a corresponding one or more encryption keys, each dataset comprising signal information.

The signal information of each dataset may be any suitable information signal. As an example, the information signal may comprise raw data produced by a nanopore sequencer, the raw data indicative of a polynucleotide sequence. Each dataset may relate to a different subject. For example, a first dataset of the data package may relate to a first human subject, a second dataset of the data package may relate to a second human subject, a third dataset of the data package may relate to a plant and so on.

At 1120, the mining node 120 uses the encryption key associated with each dataset to execute computer-readable instructions to convert the signal information of each dataset to a corresponding encrypted data output. The encrypted data output may be representative of an encoded polynucleotide sequence. The encoded polynucleotide sequence may be represented by a sequence of letters other than the IUPAC nucleotide code for the base, where the sequence of letters is determined by the encryption key (for example by reference to a look-up table). The encoded polynucleotide sequence may be represented by decoy features, such as inserting one or more random bases in a predictable pattern determined from the encryption key.

At 1130, the mining node communicates the encrypted data outputs to an authority server 130 for verification and for use in establishing a proof-of-work for a block of the blockchain.

Concerning the encryption referred to in relation to FIGS. 9, 10 and 11 and throughout this specification, the skilled person would appreciate that any suitable form of encryption and decryption will suffice, so long as it ensures that sensitive information may be hidden from the mining nodes. For example, an authority server such as authority server 130*a* may generate a first encryption key in relation to a first dataset for use by a mining node, the first encryption key and corresponding first decryption key concerning a first way of processing signal information of the first dataset. As an example, the encryption key may prescribe that the mining node converts the signal information of the first dataset into a first sequence of encoded characters (which may correspond to, for example, a polynucleotide sequence having had a first substitution cipher applied). A second encryption key and corresponding second decryption key concerning a second way of processing signal information of a second dataset may be generated, the second encryption key prescribing that the mining node convert the signal information of the second dataset into a second sequence of encoded characters (which may correspond to, for example, a polynucleotide sequence having had a second substitution cipher applied). That is, the encoding method prescribed may vary on a dataset-by-dataset basis and/or a data package-by-data package basis. Thus the encrypted data output related to one dataset may have been encrypted according to one substitution and an encrypted data output related to another dataset may have been encrypted according to another substitution. Such an approach makes it even more difficult for a mining node to determine what the information being processed may relate to. The skilled person would appreciate that the encoding/decoding methods may comprise other encryption steps and transformations besides the application of substitution ciphers.

Variations of the described embodiments are envisaged, for example, the features of all the disclosed embodiments may be combined in any way. As will be appreciated by the skilled person, the methods described herein can be used to process any suitable, large data problems, in which several datasets can be processed independently.

In the preceding detailed description, many of the processing tasks described have concerned the conversion of signal information representative of a polynucleotide sequence into a base sequence. However, the skilled person would appreciate that the methods and apparatuses described herein are applicable to other types of signal information. For example, signal information may relate to other native molecules such as proteins or secondary modifications. As another example, signal information may relate to modified or synthetic molecules such as oligonucleotide tags, analogs of nucleic acids, or expandomers including expandable nucleoside triphosphate.

A blockchain may include any form of electronic, computer-based, distributed ledger, including permissioned and un-permissioned ledgers, shared ledgers and variations thereof.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

What is claimed is:

1. A method for appending a block record to a blockchain stored on mining nodes of a network, the block record comprising payload data, a proof-of-work, and a unique identifier of a preceding block record of the blockchain, wherein the method comprises:
receiving a data package from an authority server, the data package comprising a plurality of datasets, wherein each dataset of the plurality of datasets comprises signal information, wherein the signal information of each dataset is representative of a polynucleotide sequence, and wherein the signal information representative of a polynucleotide sequence comprises raw data produced by a nanopore sequencer, the raw data comprising current information corresponding to current flow through a nanopore and a polynucleotide translocating through the nanopore;
analyzing the data package to convert the signal information of each dataset to a corresponding data output, wherein converting the signal information of each dataset to a corresponding data output comprises converting the signal information of each dataset to a corresponding read that describes the polynucleotide sequence of the signal information; and
communicating one or more of the data outputs to the authority server, the plurality of data outputs for use in establishing the proof-of-work for appending the block record to the blockchain.

2. The method of claim 1, further comprising:
receiving a signed token from the authority server;
creating the block record for the blockchain using the signed token as the proof-of-work; and
communicating the created block record to at least one mining node of the network.

3. The method of claim 2, wherein the signed token comprises a signed hash of the analyzed data package.

4. The method of claim 2, wherein creating the block record for the blockchain includes:
consulting a version of the blockchain stored in one or more machine readable storage media to extract the unique identifier of the preceding block record of the blockchain; and
retrieving the payload data from a data pool of unprocessed payload data.

5. The method of claim 1, wherein the polynucleotide sequence comprises a deoxyribonucleic acid, DNA, sequence or a ribonucleic acid, RNA, sequence.

6. The method of claim 1, wherein:
the unique identifier of the preceding block record of the blockchain comprises a hash of the preceding block record of the blockchain or a hash of a header of the preceding block of the blockchain; or
the payload data comprises at least one of transaction data or a smart contract.

7. The method of claim 1, wherein the authority server is not a mining node of the network.

8. The method of claim 1, wherein:
the data package further comprises an encryption key;
analyzing the data package to convert the signal information of each dataset to the corresponding data output comprises processing a first set of instructions using the received encryption key to convert the signal information of each dataset to a corresponding encrypted data output; and
communicating the plurality of data outputs to the authority server comprises communicating a plurality of the encrypted data outputs to the authority server, the plurality of the encrypted data outputs for use in establishing the proof-of-work for appending the block record to the blockchain.

9. A non-transitory computer readable storage medium having executable instructions stored thereon, wherein when executed by a processor, causes the processor to:
receive a data package from an authority server, the data package comprising a plurality of datasets, wherein each dataset of the plurality of datasets comprises signal information, wherein the signal information of each dataset is representative of a polynucleotide sequence, and wherein the signal information representative of a polynucleotide sequence comprises raw data produced by a nanopore sequencer, the raw data comprising current information corresponding to current flow through a nanopore and a polynucleotide translocating through the nanopore;
analyze the data package to convert the signal information of each dataset to a corresponding data output, wherein converting the signal information of each dataset to a corresponding data output comprises converting the signal information of each dataset to a corresponding read that describes the polynucleotide sequence of the signal information; and
communicate one or more of the data outputs to the authority server, the plurality of data outputs for use in establishing the proof-of-work for appending a block record to the blockchain.

10. A computing apparatus for appending a block record to a blockchain stored on mining nodes of a network, the block record comprising payload data, a proof-of-work, and a unique identifier of a preceding block of the blockchain, wherein the computing apparatus comprises:
one or more processors; and
one or more machine readable storage media having instructions stored thereon which, when processed by the one or more processors, cause the one or more processors to:
receive a data package from an authority server, the data package comprising a plurality of datasets, wherein each dataset of the plurality of datasets comprises signal information, wherein the signal information of each dataset is representative of a polynucleotide sequence, and wherein the signal information representative of a polynucleotide sequence comprises raw data produced by a nanopore sequencer, the raw data comprising current information corresponding to current flow through a nanopore and a polynucleotide translocating through the nanopore;
analyze the data package to convert the signal information of each dataset to a corresponding data output, wherein converting the signal information of each dataset to a corresponding data output comprises converting the signal information of each dataset to a corresponding read that describes the polynucleotide sequence of the signal information; and communicate a plurality of the data outputs to the authority server, the plurality of data outputs for use in establishing the proof-of-work for appending the block record to the blockchain.

11. A method, the method performed by an authority server, the authority server trusted by a plurality of mining nodes of a network to authenticate a block record of a blockchain, the method comprising:

receiving information containing a first plurality of data outputs from a first mining node of the plurality of mining nodes, each data output of the first plurality of data outputs determined from a first data package analyzed by the first mining node, the first data package comprising a plurality of datasets;

verifying the first plurality of data outputs, wherein verifying the first plurality of data outputs comprises determining that a corroboration condition has been met, wherein determining that a corroboration condition has been met comprises determining that each data output of the first plurality of data outputs has been corroborated by a threshold number of the plurality of mining nodes;

wherein determining that each data output of the first plurality of data outputs has been corroborated by a threshold number of the plurality of mining nodes comprises:

comparing the first plurality of data outputs with one or more further pluralities of data outputs, each of the one or more further pluralities of data outputs received from a corresponding mining node of the plurality of mining nodes; and wherein the one or more further pluralities of data outputs have been determined from further data packages analyzed by the corresponding mining nodes, the further data packages each containing a plurality of datasets, the plurality of datasets each comprising signal information, and one or more of the plurality of datasets overlapping with the datasets comprised within the first data package; and in response to verifying the first plurality of data outputs, digitally signing a unique token to be used as a proof-of-work in the block record of the blockchain.

12. The method of claim 11, further comprising:
sending the signed unique token to the first mining node to be used as the proof-of-work in the block record of the blockchain.

13. The method of claim 11, wherein determining that each data output of the first plurality of data outputs has been corroborated by a threshold number of the plurality of mining nodes comprises determining that each data output of the first plurality of data outputs has been corroborated within a predefined error threshold by the threshold number of the plurality of mining nodes.

14. The method of claim 11, wherein receiving information containing a first plurality of data outputs is in response to:

communicating a data package to the first mining node, the data package comprising a plurality of datasets, wherein each dataset of the plurality of datasets comprises signal information for conversion to a data output; and wherein communicating the data package to the first mining node is in response to receiving a request for the data package from the first mining node.

15. The method of claim 14, further comprising, prior to communicating a data package to the first mining mode:

receiving multiple pre-processed data items from multiple data sources; and dividing the multiple pre-processed data items into independently processable datasets;

packaging a selection of the independently processable datasets into a data package; and storing metadata concerning which of the independently processable datasets are included in the data package.

16. The method of claim 11, wherein:
the first data package analyzed by the first mining node also comprises decoy datasets; and verifying the first plurality of data outputs includes checking decoy data outputs of the first plurality of data outputs against a local register of data outputs.

17. A non-transitory computer readable storage medium having executable instructions stored thereon, wherein when executed by a processor, causes the processor to:

receive information containing a first plurality of data outputs from a first mining node of the plurality of mining nodes, each data output of the first plurality of data outputs determined from a first data package analyzed by the first mining node, the first data package comprising a plurality of datasets;

verify the first plurality of data outputs, wherein verifying the first plurality of data outputs comprises determining that a corroboration condition has been met, wherein determining that a corroboration condition has been met comprises determining that each data output of the first plurality of data outputs has been corroborated by a threshold number of the plurality of mining nodes;

wherein determining that each data output of the first plurality of data outputs has been corroborated by a threshold number of the plurality of mining nodes comprises:

compare the first plurality of data outputs with one or more further pluralities of data outputs, each of the one or more further pluralities of data outputs received from a corresponding mining node of the plurality of mining nodes; and wherein the one or more further pluralities of data outputs have been determined from further data packages analyzed by the corresponding mining nodes, the further data packages each containing a plurality of datasets, the plurality of datasets each comprising signal information, and one or more of the plurality of datasets overlapping with the datasets comprised within the first data package; and in response to verifying the first plurality of data outputs, digitally sign a unique token to be used as a proof-of-work in the block record of the blockchain.

18. An authority server, the authority server trusted by mining nodes of a network to authenticate a block record of a blockchain, each mining node comprising computing apparatuses for appending the block record to the blockchain, the authority server comprising:

one or more processors; and
one or more memory units, the memory units having instructions stored therein which, when processed by the one or more processors, cause the one or more processors to:

receive information containing a first plurality of data outputs from a first mining node of the network, each data output of the first plurality of data outputs determined from a first data package analyzed by the first mining node, the data package comprising a plurality of datasets;

verify the first plurality of data outputs, wherein verifying the first plurality of data outputs comprises determining that a corroboration condition has been met, wherein determining that a corroboration condition has been met comprises determining that each data output of the first plurality of data outputs has been corroborated by a threshold number of the plurality of mining nodes;

wherein determining that each data output of the first plurality of data outputs has been corroborated by a threshold number of the plurality of mining nodes comprises:

comparing the first plurality of data outputs with one or more further pluralities of data outputs, each of the one or more further pluralities of data outputs received from a corresponding mining node of the plurality of mining nodes; and wherein the one or more further pluralities of data outputs have been determined from further data packages analyzed by the corresponding mining nodes, the further data packages each containing a plurality of datasets, the plurality of datasets each comprising signal information, and one or more of the plurality of datasets overlapping with the datasets comprised within the first data package; and in response to verifying a first plurality of reads, digitally sign a unique token to be used as a proof-of-work in the block record of the blockchain.

19. A system for processing signal information as a proof-of-work for appending a block record to a blockchain, the system comprising:

one or more authority servers, each comprising one or more processors; and a network of mining nodes, wherein each mining node comprises one or more processors; and wherein a mining node is configured to:

receive a data package from an authority server, the data package comprising a plurality of datasets, wherein each of the plurality of datasets comprises signal information, wherein the signal information of each dataset is representative of a polynucleotide sequence, and wherein the signal information representative of a polynucleotide sequence comprises raw data produced by a nanopore sequencer, the raw data comprising current information corresponding to current flow through a nanopore and a polynucleotide translocating through the nanopore;

analyze the data package to convert the signal information of each dataset to a corresponding data output, wherein converting the signal information of each dataset to a corresponding data output comprises converting the signal information of each dataset to a corresponding read that describes the polynucleotide sequence of the signal information;

communicate a plurality of the data outputs to the authority server;

receive a signed unique token from the authority server;

create the block record for the blockchain using the signed unique token as the proof-of-work; and communicate the created block record to at least a second mining node of the network; and wherein the authority server is configured to:

receive information containing the plurality of data outputs from the mining node;

verify the plurality of data outputs, wherein verifying the first plurality of data outputs comprises determining that a corroboration condition has been met, wherein determining that a corroboration condition has been met comprises determining that each data output of the first plurality of data outputs has been corroborated by a threshold number of the plurality of mining nodes;

wherein determining that each data output of the first plurality of data outputs has been corroborated by a threshold number of the plurality of mining nodes comprises:

comparing the first plurality of data outputs with one or more further pluralities of data outputs, each of the one or more further pluralities of data outputs received from a corresponding mining node of the plurality of mining nodes; and wherein the one or more further pluralities of data outputs have been determined from further data packages analyzed by the corresponding mining nodes, the further data packages each containing a plurality of datasets, the plurality of datasets each comprising signal information, and one or more of the plurality of datasets overlapping with the datasets comprised within the first data package;

in response to verifying the plurality of data outputs, digitally sign a unique token; and send the signed unique token to the mining node to be used as the proof-of-work in the block record of the blockchain.

* * * * *